United States Patent
Tani

(10) Patent No.: US 10,035,753 B2
(45) Date of Patent: Jul. 31, 2018

(54) METHOD FOR CONTINUOUSLY PRODUCING KETOMALONIC ACID COMPOUND USING FLOW REACTOR

(71) Applicant: IHARA CHEMICAL INDUSTRY CO., LTD., Tokyo (JP)

(72) Inventor: Shinki Tani, Fuji (JP)

(73) Assignee: Kumiai Chemical Industry Co., Ltd., Tokyo (JP)

(*) Notice: Subject to any disclaimer, the term of this patent is extended or adjusted under 35 U.S.C. 154(b) by 0 days.

(21) Appl. No.: 15/119,310

(22) PCT Filed: Feb. 6, 2015

(86) PCT No.: PCT/JP2015/053334
§ 371 (c)(1),
(2) Date: Aug. 16, 2016

(87) PCT Pub. No.: WO2015/122361
PCT Pub. Date: Aug. 20, 2015

(65) Prior Publication Data
US 2017/0008829 A1 Jan. 12, 2017

(30) Foreign Application Priority Data

Feb. 17, 2014 (JP) .................. 2014-027231

(51) Int. Cl.
*C07C 67/313* (2006.01)
*C07C 67/31* (2006.01)
(Continued)

(52) U.S. Cl.
CPC ............ *C07C 67/313* (2013.01); *B01J 14/00* (2013.01); *B01J 19/1818* (2013.01);
(Continued)

(58) Field of Classification Search
None
See application file for complete search history.

(56) References Cited

U.S. PATENT DOCUMENTS

| | | | |
|---|---|---|---|
| 4,296,114 A | 10/1981 | Appleton et al. | |
| 4,584,145 A | 4/1986 | Santi et al. | |

(Continued)

FOREIGN PATENT DOCUMENTS

| | | |
|---|---|---|
| JP | 61-12647 A | 1/1986 |
| JP | 8-151346 A | 6/1996 |

(Continued)

OTHER PUBLICATIONS

Henkel ("Reactor Types and Their Industrial Applications" Ullmann's Encyclopedia of Industrial Chemistry, published online Jun. 15, 2000, DOI: 10.1002/14356007.b04_087, p. 293-327).*

(Continued)

*Primary Examiner* — Jafar Parsa
*Assistant Examiner* — Amy C Bonaparte
(74) *Attorney, Agent, or Firm* — Westerman, Hattori, Daniels & Adrian

(57) ABSTRACT

The purpose of the present invention is to provide a method for continuously producing a ketomalonic acid compound such as a ketomalonic acid diester or a hydrate thereof, which is an industrially useful compound, on an industrial scale and in a safe and steady manner. The present invention relates to: a method in which a malonic acid diester, a carboxylic acid compound and a chlorous acid compound are used as raw material compounds, and these raw material compounds are mixed together to prepare a mixture and the mixture is supplied to a flow reactor continuously, thereby continuously producing a corresponding ketomalonic acid diester or a hydrate thereof; and a continuous production apparatus for performing the method.

16 Claims, 3 Drawing Sheets

(51) Int. Cl.
  *B01J 14/00* (2006.01)
  *B01J 19/18* (2006.01)
(52) U.S. Cl.
  CPC ..... *C07C 67/31* (2013.01); *B01J 2219/00033* (2013.01); *B01J 2219/00051* (2013.01)

(56) References Cited

U.S. PATENT DOCUMENTS

| 6,329,389 | B1 | 12/2001 | Suzuki et al. |
| 6,348,461 | B1 | 2/2002 | Takano et al. |
| 8,859,803 | B2* | 10/2014 | Tani ................. C07C 67/31 560/176 |
| 2012/0004443 | A1 | 1/2012 | Tani |

FOREIGN PATENT DOCUMENTS

| WO | 2005/021547 A2 | 3/2005 |
| WO | 2010/150548 A1 | 12/2010 |
| WO | 2015/0008629 A1 | 1/2015 |

OTHER PUBLICATIONS

Gordon ("Minimizing Chlorite Ion and Chlorate Ion in Water Treated with Chlorine Dioxide" Research and Technology, Journal AWWA, Apr. 1990, p. 160-165).*
International Search Report dated Apr. 21, 2015, issued in counterpart International Application No. PCT/JP2015/053334 (2 pages).
Clark-Lewis et al., "79. Quinoxaline Derivatives. Part IV. Dihydrooxo-1 : 4 : 5-triaza-naphthalenecarboxyureides and Related spiroHydantoins" J. Chem. Soc., 1957, pp. 430-439.
Harayama et al.,"Hydrolysis Products of Flavins (Isoalloxazines)", J. Chem. Soc. Perkin Transactions 1, 1987, pp. 75-83.
Astin et al., "105. Selenium Dioxide, a New Oxidising Agent. Part III. Its Reaction with Some Alcohols and Esters", J. Chem. Soc., 1933, pp. 391-394.
Dox, "X Ethyl Oxomalonate $CH_2(CO_2C_2H_5)_2 + 2N_2O_3 \rightarrow CO(CO_2C_2H_5)_2 + H_2O + 4NO$", Organic Syntheses, vol. 4, 1925, pp. 27-28.
"Encyclopedia of Reagents for Organic Synthesis" Diethyl Oxomalonate, 3711 (2001).
Liu et al., "Oxidation of α-Methyl or α-Methylene Groups in Carbonyl Compounds with Ammonium Chlorochromate", Chinese Chemical Letters, vol. 3, No. 8, 1992, pp. 585-588.
Kochergin et al., "Chemistry of nitro esters. XVII. Production of mesoxalic acid esters", Chemical Abstracts, 123: 256144, (1 page), 1994.
Saba, "Synthesis of Vicinal Trioxo Compounds by Dimethyl Dioxirane Oxidation of 2-Diaz0-1,3-Dioxo Derivatives", Synthetic Communications, 24(5), 1994, pp. 695-699.
Tietze et al.,"An Annual Publication of Satisfactory Methods for the Preparation of Organic Chemicals", Organic Syntheses, vol. 71, 1993, pp. 214-219.
International Preliminary Report on Patentability (Form PCT/IB/373) issued in counterpart International Application No. PCT/JP2015/053334, dated Aug. 23, 2016, with Form PCT/ISA/237. (7 pages).
Toda, Kiyoshi et al., Biooxidation of a Synthetic Waste by a Microbial Film Grown on the Liquid Surface in a Shallow Flow Reactor, Applied Biochemistry and Biotechnology, The Humana Press Inc., Institute of Applied Microbiology, University of Tokyo, Nov. 2, 1989, pp 139-149.
Peter, S. et al., Kinetics of catalytic hydrogenation of β-ionone and application of a presaturated one-liquid flow reactor for the production of fine chemicals, Applied Catalysis A General 286 (2005), Nov. 28, 2004, pp. 96-110.
Caravieilhes, S. et al., Transient operation of a catalytic liquid-liquid plug flow reactor for kinetics measurements, Chemical Engineering Science, 57 (2002), pp. 2697-2705, Oct. 10, 2001.
European Search Report dated Aug. 16, 2017, issued in corresponding European Patent Application No. 15748585.5.

* cited by examiner

METHOD FOR CONTINUOUSLY PRODUCING KETOMALONIC ACID COMPOUND USING FLOW REACTOR

TECHNICAL FIELD

The present invention relates to a method for continuously producing a ketomalonic acid compound such as a ketomalonic acid diester by reacting a malonic acid compound such as a malonic acid diester with a chlorite.

BACKGROUND ART

Ketomalonic acid diesters are derivatives of malonic acid having a keto group, and are compounds to be important intermediates in an organic synthesis. In particular, ketomalonic acid diesters are useful compounds as raw materials in the production of pyrazine-2-one-3-carboxylic acid ester derivatives by the reaction with diamines (see Patent Documents 1 to 4 and Non Patent Documents 1 and 2). This reaction is utilized in the manufacture of pharmaceuticals, agricultural chemicals, and the like particularly as a method for producing quinoxalinone derivatives from aromatic diamines.

Conventionally, direct or indirect methods have been reported as the method of synthesizing ketomalonic acid diesters from malonic acid diesters. However, they all have a problem. As the method of a synthesizing ketomalonic acid diesters from malonic acid diesters, for example, a method is known in which a ketomalonic acid diester is produced by oxidizing a malonic acid diester with an oxidizing agent such as selenium dioxide (for example, see Non Patent Document 3), dinitrogen trioxide (for example, see Non Patent Document 4), or chromium trioxide (for example, see Non Patent Document 6). However, they also all have a problem such as severe toxicity of reagents, a difficulty in handling of reagents, and the like.

In addition, methods of producing a ketomalonic acid diester such as a method in which a compound obtained by substituting the active methylene moiety of a malonic acid diester with bromine is reacted with silver nitrate (for example, see Non Patent Document 7), a method in which a compound obtained by substituting the active methylene moiety of a malonic acid diester with an azo group is reacted with dimethyldioxirane (for example, see Non Patent Document 8), a method in which a compound obtained by substituting the active methylene moiety of a malonic acid diester with a methylene group is reacted with ozone (for example, see Non Patent Documents 5 and 9), and a method in which a compound obtained by substituting the active methylene moiety of a malonic acid diester with a hydroxyl group is reacted in the presence of a noble metal catalyst (for example, see Patent Document 5), and the like are also known. However, in these methods, there is a drawback that tartronic acid that is much more expensive than malonic acid diesters is used as a raw material or the active methylene moiety of a malonic acid diester is required to be modified in advance. Hence, these methods have economic and operational problems. In addition, these methods have a problem that expensive reagents, special reactants, expensive catalysts, or transition metals are used, or the like.

Furthermore, a method in which a malonic acid diester is reacted with a chlorite has been reported (see Patent Document 6). The method described in Patent Document 6 is superior to conventional methods known earlier than Patent Document 6, but it has been found out that it has a number of problems to be solved in order to implement the method on an industrial scale.

CITATION LIST

Patent Document

Patent Document 1: U.S. Pat. No. 6,329,389 B1
Patent Document 2: U.S. Pat. No. 6,348,461 B1
Patent Document 3: U.S. Pat. No. 4,296,114 A
Patent Document 4: WO 2005/021547 A2
Patent Document 5: JP 8-151346 A
Patent Document 6: WO 2010/150548 A1

Non Patent Document

Non Patent Document 1: J. W. Clark-Lewis, et al., J. Chem. Soc., 1957, 430-439.
Non Patent Document 2: Fumio Yoneda, et al., J. Chem. Soc. Perkin Transactions 1, 1987, 75-83.
Non Patent Document 3: S. Astin et al., J. Chem. Soc., 1933, 391-394.
Non Patent Document 4: A. W. Dox, Organic Syntheses, 4, 1925, 27-28.
Non Patent Document 5: Encyclopedia of Reagents for Organic Synthesis, 3711 (2001).
Non Patent Document 6: Liang Xian liu et al., Chinese Chemical Letters, 3, 1992, 585-588.
Non Patent Document 7: Chem. Abstr., 123: 256144.
Non Patent Document 8: Antonio Saba, Synthetic Communications, 24, 695-699 (1994).
Non Patent Document 9: Lutz F., et al., Organic Syntheses, 71, 214-219 (1993).

SUMMARY OF THE INVENTION

Problems to be Solved by the Invention

The present inventors have investigated the industrial production method by the method described in Patent Document 6, and have found a problem that there are not only a possibility of explosion in the implementation of the method on the scaled-up industrial scale and environmental pollution but also an operation on a safe and stable industrial scale is significantly difficult. The present inventors have investigated the cause of the explosion in detail, and it has been revealed that a great amount of explosive chlorine dioxide is generated in the reaction system and it has been found out that the explosion occurs by the chlorine dioxide. In addition, the yield significantly decreases when the reaction is conducted while removing the chlorine dioxide generated during the reaction, and thus it is not possible to solve the problem by only removing the chlorine dioxide from the reaction system.

Accordingly, the present inventors have attempted a continuous reaction on a microscale using microreactors. The reaction in a microreactor is a small scale, and thus not only it is relatively safe since the explosion is limited to a small scale even if there is an explosion but also it is superior to a batch type reaction in the mixing performance and the like. Hence, the method described in Patent Document 6 was conducted by using a microreactor having a groove diameter of about 200 micrometers, but a preferable result was not obtained as the conversion ratio was 0%. The conversion ratio was only about 1% even though the reaction temperature was set to 100° C. or higher.

An object of the present invention is to provide a method for continuously producing a ketomalonic acid compound such as an industrially useful ketomalonic acid diester or a hydrate thereof on an industrial scale and a production apparatus for that.

Another object of the present invention is to provide a method for safely, stably, and continuously producing a ketomalonic acid compound such as an industrially useful ketomalonic acid diester or a hydrate thereof on an industrial scale and a production apparatus for that.

Still another object of the present invention is to provide a method for safely, stably, and continuously producing a ketomalonic acid compound such as an industrially useful ketomalonic acid diester or a hydrate thereof at a high conversion ratio or a high yield on an industrial scale and a production apparatus for that.

Means to Solving the Problems

In view of the situation described above, the present inventors have further carried out extensive investigations on the industrial production method of ketomalonic acid compounds such as a ketomalonic acid diester or hydrates thereof in a great amount by reacting malonic acid diesters with a chlorite, and as a result, it has been found out that there is an induction period in this chemical reaction and thus the reaction does not sufficiently proceed in a short residence time by only simply mixing the raw materials, and further, a risk of a great scale explosion is low even if the reaction is conducted at a high temperature, and the reaction sufficiently proceeds in a short residence time at a high temperature in the case of using a relatively small reactor tube. In addition, it has been found out that the reaction of malonic acid diesters with a chlorite has two or more steps, and a high temperature is required in order to initiate the first step of the reaction in a short time, and the reaction can be efficiently continuously conducted by flow reactor(s) within a short residence time by raising the temperature of the raw materials to a high temperature in a short time, whereby the present invention has been completed.

In addition, although it is considered that gas is generated during the reaction and the reaction mixture is present as a gas-liquid mixture in this chemical reaction, the present inventors have surprisingly found out that it is possible to safely, stably, and continuously conduct the reaction even though the reaction is allowed to proceed in a reactor tube having a relatively great diameter.

In other words, the present invention relates to a method in which malonic acid diesters, carboxylic acid compounds, and a chlorous acid compound are used as raw material compounds, and corresponding ketomalonic acid diesters or hydrates thereof are continuously produced by mixing these raw material compounds and continuously supplying the mixture of these to flow reactor(s).

The present invention relates to said continuous production method in which the flow reactor is one or two or more tubular flow reactors.

In more detail, the present invention relates to a continuous production method comprising:

(A) a process of mixing a malonic acid diester, a carboxylic acid compound, and a chlorous acid compound;
(B) a process of supplying the mixture to flow reactor(s); and
(C) a process of reacting the mixture in the flow reactor(s),
which is for continuously producing a corresponding ketomalonic acid diester or a hydrate thereof.

The present invention relates to said continuous production method in which the flow reactor is one or two or more flow reactors, in more detail, tubular flow reactors.

In addition, the present invention relates to a continuous production method comprising said processes (A) to (c), which further comprising:

(D) a process of further aging the reaction mixture obtained in the process of reacting the mixture, which is for continuously producing a corresponding ketomalonic acid diester or a hydrate thereof.

The present invention relates to said continuous production method in which the aging process (D) is performed in one or two or more tubular flow reactors.

In addition, the present invention relates to said continuous production method in which the aging process (D) is a cooling process by air cooling, water cooling, or the like.

In addition, the present invention relates to a continuous production method comprising said processes (A) to (C) or said processes (A) to (D), which further comprising:

(E) a process of quenching the reaction,
which is for continuously producing a corresponding ketomalonic acid diester or a hydrate thereof.

The present invention relates to said continuous production method in which the quenching process (E) is performed by supplying a quench liquid through a T-shaped tube and the like.

In addition, the present invention relates to said continuous production method in which the quenching process (E) is performed in one or two or more tubular flow reactors.

The present invention relates to said continuous production method in which the quenching process (E) is a cooling process by air cooling, water cooling, or the like.

In addition, the present invention relates to said continuous production method in which the quench liquid is an aqueous solution of a sulfite and/or an alkali metal hydroxide.

In addition, the present invention relates to a continuous production method comprising said processes (A) to (C), said processes (A) to (C) and (E), said processes (A) to (D), or said processes (A) to (E), which further comprising:

(F) a process of separating a ketomalonic acid diester or a hydrate thereof from the reaction mixture thus obtained, which is for continuously producing a corresponding ketomalonic acid diester or a hydrate thereof.

The present invention relates to said continuous production method in which the separation process (F) is performed by an extraction treatment using an extraction solvent.

In addition, the present invention relates to said continuous production method in which the separation process (F) further includes a purification process.

In more detail, the present invention relates to said continuous production method in which said malonic acid diester is a malonic acid diester represented by the following general formula (1).

[Chemical formula 1]

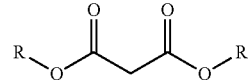

(1)

(wherein R may be the same as or different from each other and represents an alkyl group which optionally has substituent(s), a cycloalkyl group which optionally has substituent(s), an aromatic hydrocarbon group which optionally has substituent(s), or an aromatic heterocyclic group which optionally has substituent(s), and two Rs may bind to each other to form a ring with adjacent oxygen atoms).

In addition, the present invention relates to said continuous production method in which said corresponding ketomalonic acid diester is a ketomalonic acid diester represented by following general formula (2).

[Chemical Formula 2]

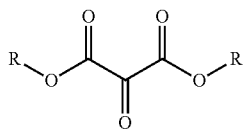

(2)

(wherein R is the same as described above).

Furthermore, the present invention relates to a continuous production apparatus, characterized in that the apparatus comprising:

(G) a mixing part configured to mix a malonic acid diester, a carboxylic acid compound, and a chlorous acid compound;

(H) a temperature rising part configured to raise the temperature of the mixture; and (I) a reaction part configured to react the mixture having a temperature raised by the temperature rising part, which is for continuously producing a corresponding ketomalonic acid diester or a hydrate thereof from the malonic acid diester as a raw material compound,
wherein the temperature rising part (H) and the reaction part (I) are one or two or more tubular flow reactors.

The present invention relates to said continuous production apparatus in which the mixing part (G) includes a mixing part configured to mix a carboxylic acid compound with a chlorous acid compound and another mixing part configured to mix a mixture thus mixed with a malonic acid diester.

The present invention relates to said continuous production apparatus in which the mixing part (G) includes a mixing part configured to mix a malonic acid diester with a carboxylic acid compound and another mixing part configured to mix a mixture thus mixed with a chlorous acid compound.

In addition, the present invention relates to said continuous production apparatus in which the mixing part (G) includes a mixing part configured to mix a chlorous acid compound with a mixture of a malonic acid diester and a carboxylic acid compound.

In addition, the present invention relates to said continuous production apparatus, comprising:

(J) an aging part configured to further age the reaction mixture obtained in the process of reacting the mixture in addition to said parts of (G) to (I),
wherein the aging part is one or two or more tubular flow reactors.

In addition, the present invention relates to said continuous production apparatus comprising said parts of (G) to (I) or said parts of (G) to (J), which further comprising:

(K) a quenching part configured to quench the reaction, wherein the quenching part is one or two or more tubular flow reactors.

The present invention relates to said continuous production apparatus in which the quenching part (K) includes a device configured to supply a quench liquid such as a T-shaped tube and the like.

In addition, the present invention relates to said continuous production apparatus comprising said parts of (G) to (I), said parts of (G) to (I) and (K), said parts of (G) to (J), or said parts of (G) to (K), which further comprising:

(L) a separation part configured to separate a ketomalonic acid diester or a hydrate thereof from the reaction mixture thus obtained.

The present invention relates to said continuous production apparatus, in which said separation part (L) includes an extraction treatment part using an extraction solvent.

In addition, the present invention relates to said continuous production apparatus, in which said separation part (L) further includes a purification part.

In more detail, the present invention relates to said continuous production apparatus, in which said malonic acid diester in the continuous production apparatus of the present invention is a malonic acid diester represented by said general formula (1).

In addition, the present invention relates to said continuous production apparatus, in which said corresponding ketomalonic acid diester in the continuous production apparatus of the present invention is a ketomalonic acid diester represented by said general formula (2).

Effects of the Invention

The present invention provides an industrial production method which makes it possible to efficiently, safely, and stably produce a great amount of ketomalonic acid compounds such as a ketomalonic acid diester, and a production apparatus therefor.

The method for producing ketomalonic acid compounds such as a ketomalonic acid diester of the present invention is an industrially excellent method as it is a method in which the active methylene moiety of a malonic acid diester is not required to be modified in advance but the active methylene moiety of a malonic acid diester is directly oxidized in one step, and further it does not require special and expensive reactants, expensive catalysts, or transition metals such as a noble metal.

It has been difficult to industrially produce ketomalonic acid compounds such as a ketomalonic acid diester in a great amount by a method in which the active methylene moiety of a malonic acid diester is directly oxidized by using a chlorite, in particular, by using a chlorite in the presence of an acid since an explosive byproduct is produced and there is a risk of explosion, however, it is possible to safely, stably, continuously, and efficiently produce ketomalonic acid compounds such as a ketomalonic acid diester in a great amount according to the method of the present invention. It is provided for the first time by the present invention that the production method by the oxidation reaction of the method of the present invention can be continuously performed by controlling the risk of explosion.

In the present invention, the reaction is continuously conducted in a relatively narrow flow path, and thus the explosion is a significantly small scale and not a scale to cause a trouble to the continuous operation even if an explosion due to the explosive substance to be produced as a byproduct occurs, and it is possible to perform a stable operation.

In addition, in the present invention, a temperature rising part is provided so that the reaction stably proceeds and is continuously conducted in a relatively narrow flow path. This makes it possible to efficiently produce a target substance.

Furthermore, in the present invention, the raw materials or reagents to be used are all compounds which are widely used in the organic synthesis and safe and easily available. In addition, the apparatus of the present invention also does not require special machining and can be manufactured by using easily available materials.

In addition, in the present invention, it is possible to provide a quenching process for detoxifying the unreacted reagent or the substance of a byproduct, and thus the waste treatment is easy, the present invention is also environmentally friendly, and has high industrial utility value.

Furthermore, in the method of the present invention, a high temperature and a high pressure are not required and a mild reaction condition can be selected, and thus it is possible to continuously produce ketomalonic acid compounds such as a ketomalonic acid diester under a convenient condition that is suitable for industrialization.

In addition, in the method of the present invention, a continuous operation is possible, and thus the production unevenness occurred in the batch type operations is less likely to occur and the quality of the produced substances can be constantly maintained.

As described above, the continuous production method of the present invention is not only significantly useful as an industrial production method but also provides an industrial production method capable of stably supplying ketomalonic acid compounds such as a ketomalonic acid diester that is significantly useful as various kinds of industrial raw materials in a great amount at low cost.

DESCRIPTION OF EMBODIMENTS

Figure 1:
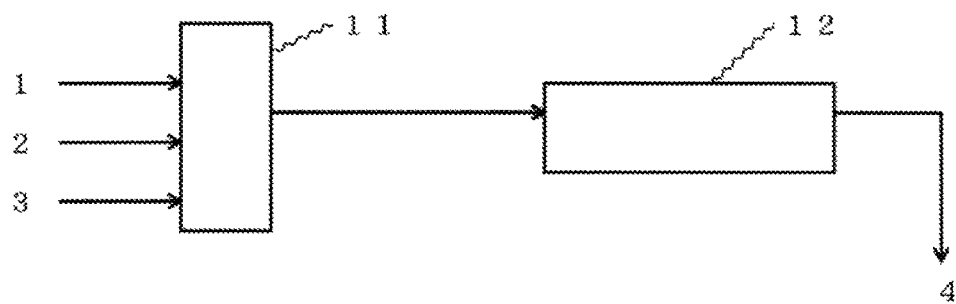
FIG. 1 schematically illustrates the outline of a reaction apparatus of the present invention. Raw material compounds are respectively supplied through raw material inlets 1 to 3 and the mixture in a mixer 11 is supplied to a tubular flow reactor 12 and the reaction is allowed to take place, and the reaction mixture after the reaction is recovered through an outlet 4.

The present invention is as follows in more detail.

[1] A method comprising:
mixing a malonic acid diester, a carboxylic acid compound, and a chlorous acid compound as raw material compounds;
continuously supplying the mixture thereof to flow reactor(s); and
continuously producing a corresponding ketomalonic acid diester or a hydrate thereof.

[2] The method according to [1], wherein mixing of the raw material compounds is performed by a process of mixing the carboxylic acid compound with the chlorous acid compound and a process of mixing the mixture with the malonic acid diester.

[3] The method according to [1], wherein mixing of the raw material compounds is performed by a process of mixing the malonic acid diester with the carboxylic acid compound and a process of mixing the mixture with the chlorous acid compound.

[4] The method according to [1], wherein mixing of the raw material compounds is performed by a process of mixing the chlorous acid compound with the mixture of the malonic acid diester and the carboxylic acid compound.

[5] The method according to any one of [1] to [4], wherein the chlorous acid compound is supplied as an aqueous solution of a chlorous acid compound.

[6] The method according to [5], wherein the concentration of the chlorous acid compound in an aqueous solution of the chlorous acid compound is from 5% by mass to 30% by mass.

[7] The method according to any one of [1] to [6], wherein the carboxylic acid compound is supplied together with a solvent.

[8] The method according to [7], wherein the solvent of the carboxylic acid compound is water.

[9] The method according to any one of [1] to [8], wherein the malonic acid diester or the mixture of the malonic acid diester and the carboxylic acid compound is supplied together with a solvent.

[10] The method according to [9], wherein the solvent is a polar solvent.

[11] The method according to [10], wherein the polar solvent is one kind or two or more kinds of polar solvents selected from the group consisting of water, acetic acid, N,N-dimethylformamide, N,N-dimethylacetamide, and N-methylpyrrolidone.

[12] The method according to any one of [9] to [11], wherein the solvent is a mixed solvent of two or more kinds of solvents.

[13] The method according to any one of [1] to [6], wherein the malonic acid diester or the mixture of the malonic acid diester and the carboxylic acid compound is supplied without a solvent.

[14] The method according to any one of [1] to [13], wherein the flow reactor(s) are one or two or more tubular flow reactors.

[15] The method according to [14], wherein the length of the tube of the tubular flow reactors is 5 m or longer.

[16] The method according to [15], wherein the length of the tube of the tubular flow reactors is from 7 m to 30 m.

[17] The method according to any one of [1] to [16], wherein the equivalent diameter of the flow reactor(s) is from 0.5 mm to 50 mm.

[18] The method according to any one of [1] to [16], wherein the equivalent diameter of the flow reactor(s) is from 0.5 mm to 10 mm.

[19] The method according to any one of [1] to [18], wherein the flow reactor(s) are provided with a temperature control part configured to control the temperature.

[20] The method according to [19], wherein the temperature control part provided to the flow reactor(s) is a bath.

[21] The method according to [19] or [20], wherein the temperature of the temperature control part provided to the flow reactor(s) is 80° C. or higher.

[22] The method according to any one of [19] to [21], wherein the temperature of the temperature control part provided to the flow reactor(s) is from 90° C. to 150° C.

[23] The method according to any one of [1] to [22], wherein the flow reactor(s) include a temperature rising part configured to raise the temperature of the mixture of raw materials and a reaction part configured to allow the mixture having a raised temperature to react.

[24] The method according to any one of [1] to [23], wherein the reaction mixture obtained in the flow reactor(s) is further supplied to second flow reactor(s) in order to be aged.

[25] The method according to [24], wherein the second flow reactor(s) are one or two or more tubular flow reactors.

[26] The method according to [24] or [25], wherein the second flow reactor (s) are cooled by air cooling, water cooling, or the like.

[27] The method according to any one of [1] to [26], wherein the reaction mixture obtained in the flow reactor(s) or the reaction mixture aged in the second flow reactor(s) is further mixed with a quench liquid for quenching the reaction and supplied to third flow reactor(s) to stop the reaction.

[28] The method according to [27], wherein the reaction mixture is mixed with a quench liquid supplied through a T-shaped tube and the like before being supplied to the third flow reactor(s).

[29] The method according to [27] or [28], wherein the third flow reactor(s) are one or two or more tubular flow reactors.

[30] The method according to any one of [27] to [29], wherein the third flow reactor(s) are cooled by air cooling, water cooling, or the like.

[31] The method according to any one of [27] to [30], wherein the quench liquid is an aqueous solution of a sulfite and/or an alkali metal hydroxide.

[32] The method according to any one of [1] to [31], wherein the ketomalonic acid diester or the hydrate thereof is further separated from the reaction mixture obtained by the method according to any one of [1] to [31].

[33] The method according to [32], wherein separation from the reaction mixture is performed by an extraction treatment using an extraction solvent.

[34] The method according to [32] or [33], wherein the separation process further includes a purification process.

[35] A continuous production method comprising:
(A) a process of mixing a malonic acid diester, a carboxylic acid compound, and a chlorous acid compound;
(B) a process of supplying the mixture to flow reactor(s); and
(C) a process of reacting the mixture in the flow reactor(s),
which is for continuously producing a corresponding ketomalonic acid diester or a hydrate thereof.

[36] The method according to [35], wherein the mixing process (A) is performed by a process of mixing the carboxylic acid compound with the chlorous acid compound and a process of mixing the mixture with the malonic acid diester.

[37] The method according to [35], wherein the mixing process (A) is performed by a process of mixing the malonic acid diester with the carboxylic acid compound and a process of mixing the mixture with the chlorous acid compound.

[38] The method according to [35], wherein the mixing process (A) is performed by a process of mixing the chlorous acid compound with a mixture of the malonic acid diester and the carboxylic acid compound.

[39] The method according to any one of [35] to [38], wherein the chlorous acid compound is supplied as an aqueous solution of a chlorous acid compound.

[40] The method according to [39], wherein the concentration of the chlorous acid compound in an aqueous solution of the chlorous acid compound is from 5% by mass to 30% by mass.

[41] The method according to any one of [35] to [40], wherein the carboxylic acid compound is supplied together with a solvent.

[42] The method according to [41], wherein the solvent of the carboxylic acid compound is water.

[43] The method according to any one of [35] to [42], wherein the malonic acid diester or the mixture of the malonic acid diester and the carboxylic acid compound is supplied together with a solvent.

[44] The method according to [43], wherein the solvent is a polar solvent.

[45] The method according to [44], wherein the polar solvent is one kind or two or more kinds of solvents selected from the group consisting of water, acetic acid, N,N-dimethylformamide, N,N-dimethylacetamide, and N-methylpyrrolidone.

[46] The method according to any one of [43] to [45], wherein the solvent is a mixed solvent of two or more kinds of solvents.

[47] The method according to any one of [35] to [40], wherein the malonic acid diester or the mixture of the malonic acid diester and the carboxylic acid compound is supplied without a solvent.

[48] The method according to any one of [35] to [47], wherein the flow reactor(s) are one or two or more tubular flow reactors.

[49] The method according to [48], wherein the length of the tube of the tubular flow reactors is 5 m or longer.

[50] The method according to [48], wherein the length of the tube of the tubular flow reactors is from 7 m to 30 m.

[51] The method according to any one of [35] to [50], wherein the equivalent diameter of the flow reactor(s) is from 0.5 mm to 50 mm.

[52] The method according to any one of [35] to [50], wherein the equivalent diameter of the flow reactor(s) is from 0.5 mm to 10 mm.

[53] The method according to any one of [35] to [52], wherein the flow reactor(s) are provided with a temperature control part configured to control the temperature.

[54] The method according to [53], wherein the temperature control part provided to the flow reactor(s) is a bath.

[55] The method according to [53] or [54], wherein the temperature of the temperature control part provided to the flow reactor(s) is 80° C. or higher.

[56] The method according to any one of [53] to [55], wherein the temperature of the temperature control part provided to the flow reactor(s) is from 90° C. to 150° C.

[57] The method according to any one of [35] to [56], wherein the method comprising:

(D) a process of further aging the reaction mixture obtained in the process of reacting the mixture in addition to the processes of (A) to (C).

[58] The method according to [57], wherein the aging process (D) is performed in one or two or more second flow reactors.

[59] The method according to [58], wherein the second flow reactor(s) are one or two or more tubular flow reactors.

[60] The method according to any one of [57] to [59], wherein the aging process (D) is a cooling process by air cooling, water cooling, or the like.

[61] The method according to any one of [35] to [60], wherein the method comprising:

(E) a process of quenching the reaction by mixing a quench liquid in addition to the processes of (A) to (C) or the processes of (A) to (D).

[62] The method according to [61], wherein the quenching process (E) is performed in one or two or more third flow reactors.

[63] The method according to [62], wherein the third flow reactors are one or two or more tubular flow reactors.

[64] The method according to any one of [61] to [63], wherein the quenching process (E) is performed by supplying a quench liquid through a T-shaped tube and the like.

[65] The method according to any one of [61] to [64], wherein the quenching process (E) is a cooling process by air cooling, water cooling, or the like.

[66] The method according to any one of [61] to [65], wherein the quench liquid is an aqueous solution of a sulfite and/or an alkali metal hydroxide.

[67] The method according to any one of [35] to [66], wherein the method comprising:

(F) a process of separating the ketomalonic acid diester or the hydrate thereof from the reaction mixture thus obtained in addition to the processes of (A) to (C), the processes of (A) to (C) and (E), the processes of (A) to (D), or the processes of (A) to (E).

[68] The method according to [67], wherein the separation process (F) is performed by an extraction treatment using an extraction solvent.

[69] The method according to [67] or [68], wherein the separation process (F) further includes a purification process.

[70] The method according to any one of [1] to [69], wherein the malonic acid diester is a malonic acid diester represented by the following general formula (1):

[Chemical formula 3]

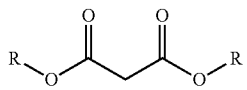

(1)

(wherein R may be the same as or different from each other and represents an alkyl group which optionally has substituent(s), a cycloalkyl group which optionally has substituent(s), an aromatic hydrocarbon group which optionally has substituent(s), or an aromatic heterocyclic group which optionally has substituent (s), and two Rs may bind to each other to form a ring with adjacent oxygen atoms).

[71] The method according to any one of [1] to [70], wherein the ketomalonic acid diester is a ketomalonic acid diester represented by following general formula (2):

[Chemical Formula 4]

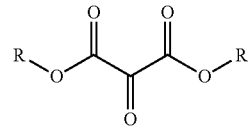

(2)

(wherein R is the same as described above).

[72] The method according to any one of [1] to [71], wherein the chlorous acid compound is a chlorite.

[73] The method according to [72], wherein the chlorite is an alkali metal salt of chlorous acid or an alkaline earth metal salt of chlorous acid.

[74] The method according to [73], wherein the alkali metal salt of chlorous acid is sodium chlorite.

[75] The method according to any one of [1] to [74], wherein the carboxylic acid compound is consisted of one kind or two or more kinds of acids selected from the group consisting of a carboxylic acid, a carboxylate, and a carboxylic anhydride.

[76] The method according to [75], wherein the carboxylic acid compound is a concurrent use of carboxylic acid and an alkali metal salt of a carboxylic acid.

[77] The method according to [75], wherein the carboxylic acid compound is a carboxylic acid.

[78] The method according to [75] or [77], wherein the carboxylic acid compound is acetic acid.

[79] A continuous production apparatus, characterized in that the apparatus comprising:

(G) a mixing part configured to mix a malonic acid diester, a carboxylic acid compound, and a chlorous acid compound;

(H) a temperature rising part configured to raise the temperature of the mixture; and (I) a reaction part configured to react the mixture having a temperature raised by the temperature rising part, which is for continuously producing a corresponding ketomalonic acid diester or a hydrate thereof from the malonic acid diester as a raw material compound, wherein the temperature rising part (H) and the reaction part (I) are one or two or more flow reactors.

[80] The continuous production apparatus according to [79], wherein the flow reactor is one or two or more tubular flow reactors.

[81] The continuous production apparatus according to [79] or [80], wherein the mixing part (G) includes a mixing part configured to mix the carboxylic acid compound with the chlorous acid compound and a mixing part configured to mix the mixture with the malonic acid diester.

[82] The continuous production apparatus according to [79] or [80], wherein the mixing part (G) includes a mixing part configured to mix the malonic acid diester with the carboxylic acid compound and a mixing part configured to mix the mixture with the chlorous acid compound.

[83] The continuous production apparatus according to [79] or [80], wherein the mixing part (G) includes a mixing part configured to mix the chlorous acid compound with a mixture of the malonic acid diester and the carboxylic acid compound.

[84] The continuous production apparatus according to any one of [80] to [83], wherein the equivalent diameter of the tubular flow reactors is from 0.5 mm to 50 mm.

[85] The continuous production apparatus according to any one of [80] to [83], wherein the equivalent diameter of the tubular flow reactors is from 0.5 mm to 10 mm.

[86] The continuous production apparatus according to any one of [80] to [85], wherein the length of the tube of the tubular flow reactors is 5 m or longer.

[87] The continuous production apparatus according to any one of [80] to [85], wherein the length of the tube of the tubular flow reactors is from 7 m to 30 m.

[88] The continuous production apparatus according to any one of [80] to [87], wherein the temperature rising part and the reaction part are present in one tubular flow reactor.

[89] The continuous production apparatus according to any one of [80] to [87], wherein the temperature rising part and the reaction part are formed in a plurality of separate tubular flow reactors, respectively.

[90] The continuous production apparatus according to any one of [79] to [89], wherein the flow reactors are provided with a temperature control part configured to control the temperature.

[91] The continuous production apparatus according to [90], wherein the temperature control part provided to the flow reactors is a bath configured to control the temperature.

[92] The continuous production apparatus according to any one of [79] to [91], wherein the apparatus comprising:

(J) an aging part configured to further age the reaction mixture obtained in the process of reacting the mixture in addition to the parts of (G) to (I).

[93] The continuous production apparatus according to [92], wherein the aging part is one or two or more flow reactors.

[94] The continuous production apparatus according to [93], wherein the flow reactors are one or two or more tubular flow reactors.

[95] The continuous production apparatus according to any one of [79] to [94], wherein the apparatus comprising:

(K) a quenching part configured to quench the reaction in addition to the parts of (G) to (I) or the parts of (G) to (J).

[96] The continuous production apparatus according to [95], wherein the quenching part is one or two or more flow reactors.

[97] The continuous production apparatus according to [96], wherein the flow reactors are one or two or more tubular flow reactors.

[98] The continuous production apparatus according to any one of [95] to [97], wherein the quenching part (K) includes a device configured to supply a quench liquid such as a T-shaped tube and the like.

[99] The continuous production apparatus according to any one of [79] to [98], wherein the apparatus comprising:

(L) a separation part configured to separate the ketomalonic acid diester or the hydrate thereof from the reaction mixture thus obtained in addition to the parts of (G) to (I), the parts of (G) to (I) and (K), the parts of (G) to (J), or the parts of (G) to (K).

[100] The continuous production apparatus according to [99], wherein the separation part (L) includes an extraction treatment part using an extraction solvent.

[101] The continuous production apparatus according to [99] or [100], wherein the separation part (L) further includes a purification part.

[102] The continuous production apparatus according to any one of [79] to [101], wherein the malonic acid diester is a malonic acid diester represented by the general formula (1).

[103] The continuous production apparatus according to any one of [79] to [102], wherein the ketomalonic acid diester is a ketomalonic acid diester represented by the general formula (2).

The terms and symbols used in the present specification will be described below.

The term "$C_a$ to $C_b$" means that the number of carbon atoms is from a to b. For example, "$C_1$ to $C_4$" means that the number of carbon atoms is from 1 to 4.

Examples of an alkyl group may include a $C_1$ to $C_6$ alkyl group and preferably a $C_1$ to $C_4$ alkyl group and the like. The $C_1$ to $C_6$ alkyl group means a straight chain or branched chain alkyl group having from 1 to 6 carbon atoms. The $C_1$ to $C_4$ alkyl group means a straight chain or branched chain alkyl group having from 1 to 4 carbon atoms. Specific examples of the alkyl group may include methyl, ethyl, propyl, isopropyl, butyl, sec-butyl, isobutyl, tert-butyl, pentyl, hexyl, and the like, preferably methyl, ethyl, propyl, isopropyl, butyl, sec-butyl, isobutyl, and tert-butyl, more preferably methyl, ethyl, propyl, and isopropyl, and even more preferably methyl and ethyl.

Examples of a cycloalkyl group may include a $C_3$ to $C_6$ cycloalkyl group and the like. The $C_3$ to $C_6$ cycloalkyl group means a cycloalkyl group having from 3 to 6 carbon atoms. Specific examples of the $C_3$ to $C_6$ cycloalkyl group may include cyclopropyl, cyclobutyl, cyclopentyl, and cyclohexyl.

Examples of an aromatic hydrocarbon group may include an aromatic hydrocarbon group having from 6 to 12 carbon atoms and the like. Specific examples of the aromatic hydrocarbon group may include phenyl, 1-naphthyl, 2-naphthyl, biphenyl, and the like. The aromatic hydrocarbon group is preferably phenyl.

Examples of an aromatic heterocyclic group may include an aromatic heterocyclic group of a 5- to 10-membered ring and preferably a 5- to 7-membered ring which has one or more (for example, from 1 to 4 and preferably 1 or 2) hetero atoms selected from a nitrogen atom, an oxygen atom, and sulfur atom other than a carbon atom. Specific examples of the aromatic heterocyclic group may include a furyl group, a thienyl group, a pyrazolyl group, a pyridyl group, a quinolinyl group, and the like. More specific examples of the aromatic heterocyclic group may include 2- or 3-furyl, 2- or 3-thienyl, 1-, 3-, 4-, or 5-pyrazolyl, 2-, 3-, or 4-pyridyl, 2- or 8-quinolyl, and the like. Preferred examples of the aromatic heterocyclic group may include 2- or 4-pyridyl, and more preferred examples thereof may include 2-pyridyl.

Examples of a haloalkyl group may include a $C_1$ to $C_4$ haloalkyl group. The $C_1$ to $C_4$ haloalkyl group means a straight chain or branched chain alkyl group that is substituted with from 1 to 9 halogen atoms to be the same as or different from one another and has from 1 to 4 carbon atoms (here, the halogen atom has the same meaning as that described above). Examples of the $C_1$ to $C_4$ haloalkyl group may include fluoromethyl, chloromethyl, bromomethyl, difluoromethyl, trifluoromethyl, chlorodifluoromethyl, 1-fluoroethyl, 2-fluoroethyl, 1-chloroethyl, 2-chloroethyl, 2,2,2-trifluoroethyl, pentafluoroethyl, 3-fluoropropyl, 3-chloropropyl, 2,2,3,3,3-pentafluoropropyl, heptafluoropropyl, 2,2,2-trifluoro-1-trifluoromethylethyl, 4-fluorobutyl, 4-chlorobutyl, 2,2,3,3,4,4,4-heptafluorobutyl, nonafluorobutyl, 2,2,2-trifluoro-1,1-di(trifluoromethyl)ethyl, and the like.

Examples of an alkoxy group may include a $C_1$ to $C_4$ alkoxy group and the like. The $C_1$ to $C_4$ alkoxy group means a ($C_1$ to $C_4$ alkyl)-O-group (here, the $C_1$ to $C_4$ alkyl has the same meaning as that described above). The $C_1$ to $C_4$ alkoxy group means methoxy, ethoxy, propoxy, isopropoxy, butoxy, sec-butoxy, isobutoxy, or tert-butoxy.

Examples of a substituent in the term "optionally has substituent(s)" may include a halogen atom, an alkyl group, a cycloalkyl group, a haloalkyl group, a hydroxyl group, an alkoxy group, an aromatic hydrocarbon group, an aromatic heterocyclic group, and the like. Here, these all have the same meanings as those described above. Examples of the substituent of the alkyl group may include a halogen atom such as chlorine, fluorine and the like, a cycloalkyl group such as a cyclohexyl group, a hydroxyl group, an alkoxy group such as a methoxy group and the like, an aromatic hydrocarbon group such as a phenyl group, and the like.

The halogen atom refers to a fluorine atom, a chlorine atom, a bromine atom, or an iodine atom.

The term "two Rs may bind to each other to form a ring with adjacent oxygen atoms" refers to that two R groups are linked to each other to form a divalent group and this divalent group forms a ring with adjacent oxygen atoms. Examples of the divalent group formed as two Rs are linked to each other may include an alkylene group having from 1 to 6 carbon atoms which optionally has substituent(s) such as a methylene group, an ethylene group, and the like. The alkylene group optionally has substituent(s) as described above, for example, a halogen atom, an alkyl group, a cycloalkyl group, a haloalkyl group, an alkoxy group, an aromatic hydrocarbon group, and the like.

(Malonic Acid Diester)

A malonic acid diester to be used as a raw material compound in the method of the present invention may be a free malonic acid, but a diester thereof is preferable from the viewpoint of ease of availability or handling. In particular, a diester form is advantageous in handling on an industrial scale, and in the method of the present invention, a representation of a malonic acid diester also includes a free malonic acid.

Next, the malonic acid diester used as a raw material of the method of the present invention and that is represented by the general formula (1) described above (hereinafter, referred to as the "raw material compound" in some cases) will be described.

R in the general formula (1) may be the same as or different from each other and represents an alkyl group which optionally has substituent(s), a cycloalkyl group which optionally has substituent(s), an aromatic hydrocarbon group which optionally has substituent(s), or an aromatic heterocyclic group which optionally has substituent(s), and two Rs may bind to each other to form a ring with adjacent oxygen atoms.

Preferred examples of R in the general formula (1) may each independently include a $C_1$ to $C_4$ alkyl group which optionally has phenyl group(s), more preferred examples thereof may include methyl, ethyl, propyl, isopropyl, and benzyl, even more preferred examples thereof may include methyl, ethyl, and benzyl, and particularly preferred examples thereof may include methyl and ethyl.

Specific examples of the malonic acid diester represented by the general formula (1) may include dimethyl malonate, diethyl malonate, dipropyl malonate, diisopropyl malonate, dibutyl malonate, diisobutyl malonate, di-sec-butyl malonate, di-tert-butyl malonate, dipentyl malonate, dihexyl malonate, dicyclopropyl malonate, dicyclopentyl malonate, dicyclohexyl malonate, diphenyl malonate, di(4-pyridyl) malonate, di(2-pyridyl)malonate, ethyl methyl malonate, methyl propyl malonate, methyl tert-butyl malonate, ethyl propyl malonate, ethyl tert-butyl malonate, methyl phenyl malonate, methyl (4-pyridyl)malonate, methyl (2-pyridyl) malonate, dibenzyl malonate, benzyl methyl malonate, benzyl ethyl malonate, and the like, but it is not limited thereto.

Preferred examples of the malonic acid diester may include dialkyl malonate which optionally has substituent(s) at the alkyl group (for example, dimethyl malonate, diethyl malonate, dipropyl malonate, diisopropyl malonate, dibutyl malonate, diisobutyl malonate, di-sec-butyl malonate, di-tert-butyl malonate, dipentyl malonate, dihexyl malonate, ethyl methyl malonate, methyl propyl malonate, methyl tert-butyl malonate, ethyl propyl malonate, ethyl tert-butyl malonate, dibenzyl malonate, benzyl methyl malonate, benzyl ethyl malonate, and the like), more preferred examples thereof may include dimethyl malonate, diethyl malonate, dipropyl malonate, diisopropyl malonate, dibutyl malonate, diisobutyl malonate, di-sec-butyl malonate, di-tert-butyl malonate, methyl tert-butyl malonate, ethyl tert-butyl malonate, dibenzyl malonate, benzyl methyl malonate, and benzyl ethyl malonate, even more preferred examples thereof may include dimethyl malonate, diethyl malonate, dipropyl malonate, diisopropyl malonate, dibutyl malonate, di-tert-butyl malonate, methyl tert-butyl malonate, ethyl tert-butyl malonate, dibenzyl malonate, benzyl methyl malonate, and benzyl ethyl malonate, even more preferred examples thereof may include dimethyl malonate, diethyl malonate, dipropyl malonate, and diisopropyl malonate, and particularly preferred examples thereof may include dimethyl malonate and diethyl malonate.

The malonic acid diester (raw material compound) represented by the general formula (1) can be a known compound or can be produced by a known method (for example, esterification of malonic acid by a usual method) from a known compound.

Incidentally, the malonic acid diester (raw material compound) represented by the general formula (1) can be used singly or as a mixture of two or more kinds of malonic acid diesters at an arbitrary proportion.

(Ketomalonic Acid Diester)

As has been described above, the malonic acid diester to be used as a raw material compound in the method of the present invention is not intended to exclude free malonic acid. Hence, the "corresponding ketomalonic acid diester" of the product by the method of the present invention also includes free ketomalonic acid as the product which corresponds to free malonic acid.

Next, the ketomalonic acid diester that is represented by the general formula (2) and a target substance to be produced by the method of the present invention will be described.

R in the general formula (2) may be the same as or different from each other and is an alkyl group which optionally has substituent(s), a cycloalkyl group which optionally has substituent(s), an aromatic hydrocarbon group which optionally has substituent(s), or an aromatic heterocyclic group which optionally has substituent(s), and two Rs may bind to each other to form a ring with adjacent oxygen atoms.

Preferred examples of R in the general formula (2) may each independently include a $C_1$ to $C_4$ alkyl group which optionally has phenyl group(s), more preferred examples thereof may include methyl, ethyl, propyl, isopropyl, and benzyl, even more preferred examples thereof may include methyl, ethyl, and benzyl, and particularly preferred examples thereof may include methyl and ethyl.

Specific examples of the ketomalonic acid diester represented by the general formula (2) may include dimethyl ketomalonate, diethyl ketomalonate, dipropyl ketomalonate, diisopropyl ketomalonate, dibutyl ketomalonate, diisobutyl ketomalonate, di-sec-butyl ketomalonate, di-tert-butyl ketomalonate, dipentyl ketomalonate, dihexyl ketomalonate, dicyclopropyl ketomalonate, dicyclopentyl ketomalonate, dicyclohexyl ketomalonate, diphenyl ketomalonate, di(4-pyridyl)ketomalonate, di(2-pyridyl)ketomalonate, ethyl methyl ketomalonate, methyl propyl ketomalonate, methyl tert-butyl ketomalonate, ethyl propyl ketomalonate, ethyl tert-butyl ketomalonate, methyl phenyl ketomalonate, methyl (4-pyridyl)ketomalonate, methyl (2-pyridyl)ketomalonate, dibenzyl ketomalonate, benzyl methyl ketomalonate and benzyl ethyl ketomalonate, and the like, but it is not limited thereto.

Preferred examples of the ketomalonic acid diester may include dialkyl ketomalonate which optionally has substituent(s) at the alkyl group (for example, dimethyl ketomalonate, diethyl ketomalonate, dipropyl ketomalonate, diisopropyl ketomalonate, dibutyl ketomalonate, diisobutyl ketomalonate, di-sec-butyl ketomalonate, di-tert-butyl ketomalonate, dipentyl ketomalonate, dihexyl ketomalonate, ethyl methyl ketomalonate, methyl propyl ketomalonate, methyl tert-butyl ketomalonate, ethyl propyl ketomalonate, ethyl tert-butyl ketomalonate, dibenzyl ketomalonate, benzyl methyl ketomalonate, benzyl ethyl ketomalonate, and the like), more preferred examples thereof may include dimethyl ketomalonate, diethyl ketomalonate, dipropyl ketomalonate, diisopropyl ketomalonate, dibutyl ketomalonate, diisobutyl ketomalonate, di-sec-butyl ketomalonate, di-tert-butyl ketomalonate, methyl tert-butyl ketomalonate, ethyl tert-butyl ketomalonate, dibenzyl ketomalonate, benzyl methyl ketomalonate, and benzyl ethyl ketomalonate, even more preferred examples thereof may include dimethyl ketomalonate, diethyl ketomalonate, dipropyl ketomalonate, diisopropyl ketomalonate, dibutyl ketomalonate, di-tert-butyl ketomalonate, methyl tert-butyl ketomalonate, ethyl tert-butyl ketomalonate, dibenzyl ketomalonate, benzyl methyl ketomalonate, and benzyl ethyl ketomalonate, even more preferred examples thereof may include dimethyl ketomalonate, diethyl ketomalonate, dipropyl ketomalonate, and diisopropyl ketomalonate, and particularly preferred examples thereof may include dimethyl ketomalonate and diethyl ketomalonate.

Incidentally, the ketomalonic acid diester represented by the general formula (2) and produced by the method of the present invention may be a single substance or a mixture thereof having an arbitrary mixing proportion.

(Hydrate)

Next, a hydrate of the ketomalonic acid diester that is represented by the general formula (2) and a target substance to be produced by the method of the present invention will be described.

The ketomalonic acid diester that is represented by the general formula (2) and produced by the method of the present invention is a compound which has a keto group between two ester groups or the like, namely, a compound which has an electron withdrawing group at the position adjacent to the keto group. Hence, the ketomalonic acid diester represented by the general formula (2) forms a hydrate of a ketomalonic acid diester represented by the following general formula (3):

[Chemical formula 5]

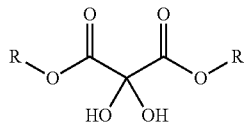

(3)

(wherein R is the same as described above.)

in the presence of water. This hydrate can be converted to a ketomalonic acid diester represented by the keto form of the general formula (2), for example, by performing a dehydration treatment such as a heating treatment and the like, if necessary. Such a reversible reaction is the same as the general nature of a hydrate such as chloral hydrate.

In general, the product is obtained in the form of the hydrate of a ketomalonic acid diester represented by the general formula (3) when the reaction of the present invention is conducted in the presence of water. On the other hand, the product is generally obtained in the form of the ketomalonic acid diester represented by the general formula (2) when the reaction of the present invention is conducted under an anhydrous condition.

Furthermore, in a case in which it is desired that the reaction of the present invention is conducted in the presence of water and the product is isolated in the form of a ketomalonic acid diester represented by the general formula (2), the product can be easily obtained in the form of the ketomalonic acid diester represented by the general formula (2) specifically by performing, for example, a dehydration treatment such as the azeotropic dehydration with toluene in post-treatment after the reaction.

In other words, in the method of the present invention, the form of the product to be isolated can be set to a desired form between the form of the ketomalonic acid diester represented by the general formula (2) or the form of the hydrate of a ketomalonic acid diester represented by the general formula (3) by appropriately selecting the reaction solvent or the method of the post-treatment after the reaction.

(Chlorous Acid Compound)

Subsequently, the chlorous acid compound to be used in the method of the present invention will be described.

In the method of the present invention, one kind or two or more kinds of chlorous acid compounds selected from chlorous acid or a chlorite are used.

As the chlorite, a salt which is formed from a chlorite ion and a cation can be presented, but it is not limited thereto.

As the cation, a metal cation or an onium cation can be exemplified, but it is not limited thereto.

Examples of the metal cation may include an alkali metal ion such as a lithium ion, a sodium ion, a potassium ion, a cesium ion, or the like; an alkaline earth metal ion such as a magnesium ion, a calcium ion, a barium ion, or the like; an earth metal ion such as an aluminum ion or the like; a zinc group ion such as a zinc ion or the like; and a transition metal ion such as a copper ion, a silver ion, a nickel ion, a manganese ion, an iron ion, or the like, but it is not limited thereto.

Examples of the onium cation may include an ammonium ion ($NH_4^+$); a quaternary ammonium ion having a straight chain or branched chain $C_1$ to $C_8$ alkyl group or a phenyl group, such as a tetramethylammonium ion, a tetrabutylammonium ion, a tetraoctylammonium ion, a trimethylbutylammonium ion, a trimethyloctylammonium ion, a tributylmethylammonium ion, a trioctylmethylammonium ion, or the like; and a quaternary phosphonium ion having a straight chain or branched chain $C_1$ to $C_8$ alkyl group or a phenyl group, such as a tetramethylphosphonium ion, a tetrabutylphosphonium ion, a tetraphenylphosphonium ion, or the like, but it is not limited thereto.

Furthermore, a salt of chlorous acid with an amine (amine salt) can also be exemplified as the chlorite.

Examples of the amine to form the salt may include methylamine, dimethylamine, trimethylamine, ethylamine, diethylamine, triethylamine, propylamine, dipropylamine, tripropylamine, butylamine, dibutylamine, tributylamine, diisopropylethylamine, hydrazine, methylhydrazine, pyridine, 2-methylpyridine, 3-methylpyridine, 4-methylpyridine, 2,4-dimethylpyridine, quinoline, aniline, N,N-diethylaniline, or the like, but it is not limited thereto.

These chlorites may be an anhydrate or a hydrate.

These chlorites may be a single salt or a double salt.

Specific examples of the chlorous acid compound may include chlorous acid; an alkali metal salt of chlorous acid including lithium chlorite, sodium chlorite, sodium chlorite trihydrate, potassium chlorite, or the like; an alkaline earth metal salt of chlorous acid including magnesium chlorite, magnesium chlorite trihydrate, calcium chlorite, calcium chlorite trihydrate, barium chlorite, barium chlorite dihydrate, or the like; an earth metal salt of chlorous acid such as aluminum chlorite, or the like; a zinc group salt of chlorous acid such as zinc chlorite dihydrate, or the like; a transition metal salt of chlorous acid such as copper(II) chlorite, copper(III) chlorite, silver chlorite, nickel chlorite dihydrate, manganese chlorite, or the like; ammonium chlorite; a quaternary ammonium salt of chlorous acid such as tetramethylammonium chlorite, or the like; a quaternary phosphonium salt of chlorous acid such as (2,4-dinitrophenyl)triethylphosphonium chlorite, or the like; an amine salt of chlorous acid such as methylamine chlorite, tripropylamine chlorite, hydrazine chlorite, pyridine chlorite, 4-methylpyridine chlorite, 2,4-dimethylpyridine chlorite, quinoline chlorite, or the like; and a double salt such as $KClO_2 \cdot NaClO_2$, $Cu(ClO_2)_2 \cdot 2KClO_2 \cdot 2H_2O$, $Cu(ClO_2)_2 \cdot Mg(ClO_2)_2 \cdot 8H_2O$, $Cu(ClO_2)_2 \cdot Ba(ClO_2)_2 \cdot 4H_2O$, or the like, but it is not limited thereto.

These chlorous acid compounds are known compounds.

These chlorous acid compounds may be used singly or as a mixture of two or more kinds thereof at an arbitrary proportion.

From the viewpoint of convenience of availability and handling, reactivity, and the like, as the chlorous acid compound, a chlorite is preferable, an alkali metal salt of chlorous acid or an alkaline earth metal salt of chlorous acid is more preferable, an alkali metal salt of chlorous acid is even more preferable, sodium chlorite or potassium chlorite is even more preferable, and it is even more preferable to use sodium chlorite.

These chlorous acid compounds can be used in any form such as a liquid or solid consisted of only a chlorous acid compound, or an aqueous solution of a chlorous acid compound, or a solution of a chlorous acid compound with a solvent other than water, or the like. As the solvent other than water, the solvents that can be used in the method of the present invention and will be described later can be exemplified, but it is not limited thereto.

From the viewpoint of convenience of availability or handling, reactivity, and the like, it is preferable to supply the chlorous acid compound as an aqueous solution. The concentration of the chlorous acid compound in the case of an aqueous solution is not particularly limited, but examples thereof may include ranges of from 5% by mass to 80% by mass, from 5% by mass to 60% by mass, from 5% by mass to 50% by mass, from 5% by mass to 40% by mass, from 5% by mass to 30% by mass, and from 5% by mass to 25% by mass, preferably from 10% by mass to 80% by mass, from 10% by mass to 60% by mass, from 10% by mass to 50% by mass, from 10% by mass to 40% by mass, from 10% by mass to 30% by mass, from 10% by mass to 25% by mass, and from 10% by mass to 20% by mass.

In the reaction of the present invention, the reaction proceeds even when the molar ratio of the chlorous acid compound used is any molar ratio with respect to the raw material compound represented by the general formula (1), but when the raw material compound is a compound represented by the general formula (1), examples of the molar ratio of the chlorous acid compound per 1 mole of the raw material compound may usually include ranges of from 1.0 to 15.0 moles, from 1.0 to 10.0 moles, and from 1.0 to 5.0 moles, preferably from 1.2 to 15.0 moles, from 1.2 to 10.0 moles, and from 1.2 to 5.0 moles, more preferably from 1.5 to 15.0 moles, from 1.5 to 10.0 moles, and from 1.5 to 5.0 moles, and even more preferably from 1.5 to 3.5 moles.

(Carboxylic Acid Compound)

It is preferable to perform the method of the present invention in the presence of a carboxylic acid compound.

Subsequently, the carboxylic acid compound in the present invention will be described.

It is preferable that the method of the present invention is performed in the presence of one kind or two or more kinds of carboxylic acid compounds selected from the group consisting of a carboxylic acid, a carboxylate, and a carboxylic anhydride as an acid.

Particularly preferred examples of the carboxylic acid compound in the method of the present invention may include a carboxylic acid. Examples of the carboxylic acid in the method of the present invention may include an organic carboxylic acid such as an aliphatic carboxylic acid, an alicyclic carboxylic acid, an aromatic carboxylic acid a heterocyclic carboxylic acid, or the like. Preferred examples of the carboxylic acid may include a carboxylic acid represented by the following general formula (4).

$$R^1\text{—COOH} \qquad (4)$$

(wherein, $R^1$ represents a hydrogen atom, an optionally substituted alkyl group, an optionally substituted cyclic alkyl group, or a phenyl group which optionally has substituent(s), or an aromatic heterocyclic group which optionally has substituent(s).)

$R^1$ in the general formula (4) represents a hydrogen atom; a straight chain or branched chain $C_1$ to $C_6$ alkyl group such as a methyl group, an ethyl group, an n-propyl group, an isopropyl group, an n-butyl group, a sec-butyl group, a t-butyl group, an n-pentyl group, an n-hexyl group, or the like (the straight chain or branched alkyl group optionally has substituent (s), for example, a straight chain or branched chain $C_1$ to $C_6$ alkyl group such as a methyl group, an ethyl group, an n-propyl group, an isopropyl group, an n-butyl group, a sec-butyl group, a t-butyl group, an n-pentyl group, an n-hexyl group, or the like; a cyclic $C_3$ to $C_6$ alkyl group such as a cyclopropyl group, a cyclobutyl group, a cyclopentyl group, cyclohexyl group, or the like; a hydroxyl group; a straight chain or branched chain $C_1$ to $C_6$ alkoxy group such as a methoxy group, an ethoxy group, an n-propoxy group, an isopropoxy group, or the like; an aryl group such as a phenyl group, or the like; or a heteroaryl group such as a pyridyl group, a furyl group, or the like, and the like); a cyclic $C_3$ to $C_6$ alkyl group such as a cyclopropyl group, a cyclobutyl group, a cyclopentyl group, a cyclohexyl group, or the like (the cyclic alkyl group optionally has substituent(s), for example, a straight chain or branched chain $C_1$ to $C_6$ alkyl group such as a methyl group, an ethyl group, an n-propyl group, an isopropyl group, an n-butyl group, a sec-butyl group, a t-butyl group, an n-pentyl group, r an n-hexyl group, or the like; a cyclic $C_3$ to $C_6$ alkyl group such as a cyclopropyl group, a cyclobutyl group, a cyclopentyl group, cyclohexyl group, or the like; a hydroxyl group; a straight chain or branched chain $C_1$ to $C_6$ alkoxy group such as a methoxy group, an ethoxy group, an n-propoxy group, an isopropoxy group, or the like; an aryl group such as a phenyl group, or the like; or a heteroaryl group such as a pyridyl group, a furyl group, or the like, and the like); a phenyl group (the phenyl group optionally has substituent(s), for example, a straight chain or branched chain $C_1$ to $C_6$ alkyl group such as a methyl group, an ethyl group, an n-propyl group, an isopropyl group, an n-butyl group, a sec-butyl group, a t-butyl group, an n-pentyl group, a n-hexyl group, or the like; a cyclic $C_3$ to $C_6$ alkyl group such as a cyclopropyl group, a cyclobutyl group, a cyclopentyl group, a cyclohexyl group, or the like; a hydroxyl group; a straight chain or branched chain $C_1$ to $C_6$ alkoxy group such as a methoxy group, an ethoxy group, an n-propoxy group, an isopropoxy group, or the like; a halogen atom such as bromine atom, chlorine atom, fluorine atom, iodine atom, or the like; an aryl group such a phenyl group, or the like; a heteroaryl group such as a pyridyl group. a furyl group, or the like, and the like); or a 5 to 7-membered heteroaryl group which has from 1 to 3 heteroatoms selected from the group consisting of an oxygen atom, a nitrogen atom, and a sulfur atom, such as a pyridyl group, a furanyl group, or the like (the heteroaryl group optionally has substituent(s), for example, a straight chain or branched chain $C_1$ to $C_6$ alkyl group such as a methyl group, an ethyl group, an n-propyl group, an isopropyl group, an n-butyl group, a sec-butyl group, a t-butyl group, an n-pentyl group, a n-hexyl group, or the like; a cyclic $C_3$ to $C_6$ alkyl group such as a cyclopropyl group, a cyclobutyl group, a cyclopentyl group, cyclohexyl group, or the like; a hydroxyl group; a straight chain or branched chain $C_1$ to $C_6$ alkoxy group such as a methoxy group, an ethoxy group, an n-propoxy group, or an isopropoxy group; a halogen atom such as bromine atom, chlorine atom, fluorine atom, iodine atom, or the like; an aryl group such as a phenyl group, or the like; or a heteroaryl group such as a pyridyl group, a furyl group, or the like).

Examples of the carboxylate in the method of the present invention may include a salt of the carboxylic acid compound represented by the general formula (4) described above. Examples of the metal atom in the metal ion to form the salt may include an alkali metal atom such as a lithium atom, a sodium atom, potassium atom, or the like; an alkaline earth metal atom such as a magnesium atom, a calcium atom, a barium atom or the like; an earth metal atom such as an aluminum atom or the like; a zinc group atom such as a zinc atom or the like; and a transition metal atom such as a copper atom, a silver atom, a nickel atom, a lead atom, a manganese atom, an iron atom, or the like, but it is not limited thereto.

In addition, examples of the onium cation to form the salt may include an ammonium ion ($NH_4^+$); and a quaternary ammonium ion having a straight chain or branched chain $C_1$ to $C_8$ alkyl group or a phenyl group, such as a tetramethylammonium ion, a tetrabutylammonium ion, a tetraoctylammonium ion, a trimethylbutylammonium ion, a trimethyloctylammonium ion, a tributylmethylammonium ion, a trioctylmethyl ammonium ion, or the like; and a quaternary phosphonium ion having a straight chain or branched chain $C_1$ to $C_8$ alkyl group or a phenyl group, such as a tetramethylphosphonium ion, a tetrabutylphosphonium ion, a tetraphenylphosphonium ion, or the like, but it is not limited thereto.

Furthermore, as the carboxylate, a salt of a carboxylic acid with an amine (an amine salt of carboxylic acid) can also be exemplified.

Examples of the amine to form the carboxylate may include methylamine, dimethylamine, trimethylamine, ethylamine, diethylamine, triethylamine, propylamine, dipropylamine, tripropylamine, butylamine, dibutylamine, tributylamine, diisopropylethylamine, pyridine, quinoline, isoquinoline, aniline, N,N-diethylaniline, or the like, but it is not limited thereto.

Examples of the carboxylic anhydride in the method of the present invention may include an anhydride of the carboxylic acid compounds represented by the general formula (4) described above. The carboxylic anhydride may be formed from only the same carboxylic acid, or it may be a carboxylic anhydride formed from different carboxylic acids. It is preferable that such a carboxylic anhydride is converted into a free carboxylic acid in water or a water-containing solvent system.

Specific examples of one kind or two or more kinds of carboxylic acid compounds selected from the group consisting of a carboxylic acid, a carboxylate, and a carboxylic anhydride in the method of the present invention may include a carboxylic acid such as acetic acid, propionic acid, or the like; an alkali metal salt of a carboxylic acid such as sodium acetate, sodium propionate, potassium acetate, potassium propionate, or the like; an alkaline earth metal salt of a carboxylic acid such as magnesium acetate, magnesium propionate, calcium acetate, calcium propionate, or the like; a quaternary ammonium salt of a carboxylic acid such as ammonium acetate, ammonium propionate, tetrabutylammonium acetate, or the like; a quaternary phosphonium salt of a carboxylic acid such as tetrabutylphosphonium acetate, or the like; an amine salt of a carboxylic acid such as triethylamine acetate, pyridine acetate, or the like; and a carboxylic anhydride such as acetic anhydride, propionic anhydride, or the like, but it is not limited thereto.

The carboxylic acid compound selected from the group consisting of a carboxylic acid, a carboxylate, and a carboxylic anhydride in the method of the present invention can be used singly, or different two or more arbitrary carboxylic acid compounds can be used in combination at an arbitrary proportion.

When the carboxylic acid compound is used singly, a carboxylic acid or a carboxylic anhydride can be exemplified as preferred one, a carboxylic acid can be exemplified as more preferred one, an aliphatic carboxylic acid such as acetic acid, and the like, or an aliphatic carboxylic anhydride such as acetic anhydride, and the like, can be exemplified as even more preferred one, and an aliphatic carboxylic acid such as acetic acid, and the like, can be exemplified as particularly preferred one, but it is not limited thereto.

When different two or more kinds of carboxylic acid compounds are used in combination, a combination of a carboxylic acid with a carboxylate can be exemplified as a preferred combination of carboxylic acid compounds, a combination of a carboxylic acid with an alkali metal salt of a carboxylic acid can be exemplified as a more preferred combination, and a combination of an aliphatic carboxylic acid with a salt thereof such as a combination of acetic acid with sodium acetate, a combination of acetic acid with potassium acetate, or the like, can be exemplified as an even more preferred combination, but it is not limited thereto.

Preferred specific examples of the carboxylic acid compound in the reaction of the present invention may include acetic acid alone, propionic acid alone, acetic anhydride alone, a combination of acetic acid with sodium acetate, a combination of acetic acid with potassium acetate, more preferred examples thereof may include acetic acid alone, a combination of acetic acid with sodium acetate, or a combination of acetic acid with potassium acetate, even more preferred examples thereof may include acetic acid alone or a combination of acetic acid with sodium acetate, and particularly preferred examples thereof may include acetic acid alone, but it is not limited thereto.

The amount of the carboxylic acid compound used in the method of the present invention may be any one as long as it is an amount in which the reaction sufficiently proceeds, but examples of the amount per 1 mole of the malonic acid diester represented by the general formula (1) may include ranges of from 0.01 to 50 moles, from 0.1 to 50 moles, and from 0.4 to 50 moles, preferably from 0.01 to 10 moles, from 0.1 to 10 moles, and from 0.4 to 10 moles, more preferably from 0.01 to 5 moles, from 0.1 to 5 moles, and from 0.4 to 5 moles, and even more preferably from 0.01 to 2 moles, from 0.1 to 2 moles, and from 0.4 to 2 moles, but a carboxylic acid can also be served as a solvent to be described below by being used in a great excess amount in the case of using a carboxylic acid as the carboxylic acid compound.

(Solvent)

The method of the present invention can be carried out in the absence of a solvent, but it can also be carried out in the presence of a solvent.

As the solvent in the method of the present invention, for example the method can be carried out in a water medium. The method can be sufficiently performed even with only the water medium derived from the aqueous solution of the chlorous acid compound in the case of using the chlorous acid compound described above as an aqueous solution. Furthermore, it can also be performed by using another solvent other than water.

Examples of the solvent other than water used in the reaction of the present invention may include a carboxylic acid (for example, acetic acid, propionic acid, and the like, and preferably acetic acid); an acid anhydride (for example, acetic anhydride, propionic anhydride, and the like, and preferably acetic anhydride); a nitrile (for example, acetonitrile, propionitrile, and the like, preferably acetonitrile); an alcohol (for example, methanol, ethanol, propanol, isopropanol, butanol, tert-butanol, ethylene glycol, and the like, and preferably methanol); a carboxylic acid ester (for example, acetic acid ester, and the like, specifically, methyl acetate, ethyl acetate, butyl acetate, and the like, and preferably ethyl acetate); a carbonic acid ester (for example, ethylene carbonate, propylene carbonate, and the like); a ketone (for example, acetone, ethyl methyl ketone, isopropyl methyl ketone, isobutyl methyl ketone (MIBK), cyclohexanone, and the like, and preferably, acetone and isobutyl methyl ketone); an amide (for example, N,N-dimethylformamide (DMF), N,N-diethylformamide, N,N-dimethylacetamide (DMAc), N-methylpyrrolidone (NMP), and the like, preferably, N,N-dimethylformamide, N,N-dimethylacetamide, and N-methylpyrrolidone, and more preferably N,N-dimethylformamide); an alkyl urea (for example, tetramethylurea, N,N'-dimethylimidazolidinone (DMI) and the like, and preferably N,N'-dimethylimidazolidinone); a phosphoric acid amide (for example, hexamethylphosphoric triamide (HMPA), and the like); a sulfoxide (for example, dimethyl sulfoxide, and the like); a sulfone (sulfolane, dimethyl sulfone, and the like); an ether (for example, tetrahydrofuran (THF), 2-methyltetrahydrofuran, 1,4-dioxane, diethyl ether, dipropyl ether, diisopropyl ether, dibutyl ether, di-tert-butyl ether, diphenyl ether, cyclopentyl methyl ether (CPME), methyl tert-butyl ether, 1,2-dimethoxyethane (DME), diglyme, and the like, and preferably tetrahydrofuran); an aromatic hydrocarbon (for example, benzene, toluene, xylene, ethylbenzene, cumene, trimethylbenzene, and the like, and preferably toluene and xylene); a halogenated aromatic hydrocarbon (for example, chlorobenzene, dichlorobenzene, trichlorobenzene, and the like, and preferably chlorobenzene); an aliphatic hydrocarbon (for example, pentane, hexane, octane, decane, dodecane, isododecane, hexadecane, isohexadecane, cyclohexane, ethylcyclohexane, methyldecalin, dimethyldecalin, and the like); a halogenated aliphatic hydrocarbon (for example, dichloromethane, chloroform, carbon tetrachloride, 1,2-dichloroethane, and the like, and preferably dichloromethane), but it is not limited thereto. These solvents can be used singly or as a mixed solvent having an arbitrary mixing proportion.

As the solvent to be used in the reaction of the present invention, it is preferable to use a polar solvent from the viewpoint of affinity, reactivity, and the like between the raw material compound and the chlorous acid compound.

The polar solvent may preferably include water, a carboxylic acid, a nitrile, a ketone, an alcohol, an ester, a carbonic acid ester, an acid anhydride, an amide, a sulfoxide, a sulfone, or a mixed solvent thereof, more preferably water, a carboxylic acid, a nitrile, an amide, a sulfone, or a mixed solvent thereof, further more preferably water, a carboxylic acid, a nitrile, an amide, or a mixed solvent thereof, even more preferably water, a nitrile, an amide, or a mixed solvent thereof, and particularly preferably water, an amide, or a mixed solvent thereof.

The polar solvent referred to herein is a solvent having a relative dielectric constant of 5 or more. Here, the relative dielectric constant is the value described in the "Chemical Handbook" (Basic), edited by the Chemical Society of Japan, 5th revised edition, pp. I-770 to 777, Maruzen, 2004.

As the solvent to be used in the method of the present invention, a polar solvent having a relative dielectric constant of 5 or more is preferable, a polar solvent having a relative dielectric constant of 7 or more is more preferable, a polar solvent having a relative dielectric constant of 17 or more is even more preferable, and a polar solvent having a relative dielectric constant of 20 or more is particularly preferable.

Specific examples of the polar solvent may include one kind or two or more kinds of polar solvents selected from the group consisting of water, acetic acid, acetonitrile, N,N-dimethylformamide, N,N-dimethylacetamide, N-methylpyrrolidone, and dimethyl sulfoxide; preferably one kind or two or more kinds of polar solvents selected from the group consisting of water, acetic acid, acetonitrile, N,N-dimethylformamide, N,N-dimethylacetamide, and N-methylpyrrolidone; more preferably one kind or two or more kinds of polar solvents selected from the group consisting of water, acetic acid, acetonitrile, and N,N-dimethylformamide; even more preferably one kind or two or more kinds of polar solvents selected from the group consisting of water, acetonitrile, and N,N-dimethylformamide; even more preferably one kind or two kinds of polar solvents selected from the group consisting of water and N,N-dimethylformamide;

and particularly preferably water or a solvent system containing water. Water is preferable since it is convenient and inexpensive.

It is preferable to conduct the reaction of the present invention in the presence of water medium since it is possible to set the form of the product to be isolated to a desired form between the form of the ketomalonic acid diester represented by the general formula (2) or the form of the hydrate of a ketomalonic acid diester represented by the general formula (3) by appropriately selecting the method of the post-treatment after the reaction.

The amount of the solvent in the reaction of the present invention may be any amount as long as the fluidity of the reaction system can be sufficiently secured, but from the viewpoint of the reactivity, suppression of a by-product, economic efficiency, and the like, examples of the amount per 1 mole of the raw material compound represented by the general formula (1) may include ranges of from 0.01 to 10 L, preferably from 0.05 to 5 L, more preferably from 0.2 to 3 L, and even more preferably from 0.5 to 2 L, but it is not limited thereto.

(Flow Reactor)

The reactor is broadly classified into the batch type and the continuous type, and the continuous reactor is a reactor for continuously performing the supply of raw materials, the reaction, and the recovery of the reaction mixture at the same time. An example of the continuous reactor is a flow reactor. The flow reactor is a reactor capable of continuously supplying the raw materials, allowing the reaction to occur continuously, and continuously recovering the reaction mixture. The flow reactor is broadly classified into the tubular flow reactor (including a tube type flow reactor) and the vessel type flow reactor, and both of them can be used for a continuous reaction.

The flow reactor of the present invention may be provided with a temperature control means to control the temperature of the flow reactor, and for example, it may be provided with a temperature control unit for heating and/or cooling. The temperature control unit may be any suitable ones, and examples of the temperature control unit may include a bath and a jacket and preferably include a bath. The mode of bath may be any suitable modes, and for example, may be a "retention type", a "fluidized type (circulation type)", an "open type", or a "closed type". In addition, the material of the flow reactor is not particularly limited as long as it is not damaged by the raw materials and the solvents, and examples thereof may include a metal (titanium, nickel, stainless steel, and various alloys such as Hastelloy C), a resin (fluorine resin), glass (silicon and quartz), porcelain (cordierite and ceramics), and the like.

A tubular flow reactor is exemplified as a preferred flow reactor although the continuous reaction of the present invention does not exclude an aspect executed in the vessel type flow reactor. The tubular flow reactor of the present invention may be those which can continuously circulate a liquid mixture or a gas-liquid mixture, and the cross-sectional shape of the tube may be any of a circular shape, a square shape, a polygonal shape, an elliptical shape, and the like, or may be a combination of these shapes. In addition, the material of the tube is not particularly limited as long as it is not damaged by the raw materials and the solvents, and examples thereof may include a metal (titanium, nickel, stainless steel, and various alloys such as Hastelloy C), a resin (fluorine resin), glass (silicon and quartz), porcelain (cordierite and ceramics), and the like, and a tube made of metal which exhibits excellent pressure resistance is preferable. The tubular flow reactor of the present invention may also be provided with a temperature control means to control the temperature, and for example, it may be provided with a temperature control unit for heating and/or cooling. The temperature control unit may be any suitable ones, and examples of the temperature control unit may include a bath, a jacket, and the like, and preferably include a bath. The mode of bath may be any suitable modes, and for example, may be a "retention type", a "fluidized type (circulation type)", an "open type", or a "closed type". The control of temperature in the reaction apparatus is easy when a flow reaction apparatus provided with a temperature control means is used, and thus it is possible to more safely perform the reaction or the treatment. As such a flow reaction apparatus, it is possible to use a reaction apparatus such as a spiral type, a shell-and-tube type, and a plate heat exchanger type.

The style of disposition the tube of the tubular flow reactor of the present invention is not particularly limited, and for example, the tube may be disposed in a straight shape, a curved shape, or a coiled shape. A tubular reactor in which the tube is disposed in a coiled shape can be preferably exemplified. In addition, the tube may be one or a bundled tube prepared by regularly or irregularly bundling two or more tubes at appropriate intervals. In the present specification, description will be given on the basis of the tubular flow reactor having one tube for convenience, but it is also possible to use a tubular flow reactor with a bundled tubes prepared by regularly or irregularly bundling a plurality of tubes of two or more at appropriate intervals in accordance with the description of the present specification in a case in which an increase in the production efficiency is desired.

In addition, the tubular flow reactor of the present invention may have a mixer if necessary. The mixer is not particularly limited as long as it has a function that can continuously mix two or more kinds of fluids such as gas and liquid or liquid and liquid, and examples thereof may include a Y-shaped mixer, a T-shaped mixer, a cross-shaped mixer, a pipeline type mixer (line mixer including a static mixer and the like), and the like. As a preferred aspect of the present invention, a method is exemplified in which all of the raw material compounds are mixed in the mixer prior to being supplied to the flow reactor and the mixture is supplied to the flow reactor, and thus it is not required to use a flow reactor including a mixer therein except the aspect of a special case.

The equivalent diameter of the tube of the tubular reactor of the present invention is not particularly limited as long as the tube has a size enough to continuously circulate liquid mixture or a gas-liquid mixture, and it is preferably 0.5 mm or more since a gaseous byproduct is produced in the chemical reaction of the present invention in some cases and also in terms of the production efficiency. In addition, a tube having a significantly great equivalent diameter is not preferable since an explosive byproduct is produced in the chemical reaction of the present invention in some cases. The preferred equivalent diameter is from 0.5 mm to 50 mm, from 0.5 mm to 30 mm, and from 0.5 mm to 10 mm, and more preferred equivalent diameter is from 1 mm to 50 mm, from 1 mm to 30 mm, from 1 mm to 10 mm, and from 3 mm to 10 mm or so.

The "equivalent diameter (De)" in the present invention is a value defined by the following Equation.

$$De=4 \cdot Af/Wp$$

(wherein Af denotes the cross-sectional area of flow path and Wp denotes the length of wetted perimeter.)

For example, the equivalent diameter of a circular-shaped tube with a radius r is as follows.

$$De = 4 \cdot \pi r^2 / 2\pi r$$
$$= 2r$$

The length of the tube of the tubular flow reactor of the present invention is not particularly limited as long as it is in the range in which the temperature of the raw material compounds can be raised and a sufficient reaction can be performed or the range in which a desired treatment can be performed, and the length can be appropriately designed in balance with the equivalent diameter of the tube. It is possible to appropriately set the length in the range of 1 m or more, 2 m or more, 3 m or more, and 5 m or more, preferably from 5 m to 50 m, from 5 m to 30 m, and from 5 m to 20 m, more preferably from 7 m to 50 m, from 7 m to 30 m, and from 7 m to 20 m, and even more preferably from 9 m to 50 m, from 9 m to 30 m, and from 9 m to 20 m, for example, in a case in which a tube having an equivalent diameter of about from 1 mm to 6 mm is used. Also, it is possible to appropriately set the length in the range of 1 m or more, 2 m or more, 3 m or more, and 5 m or more, preferably from 5 m to 50 m, from 5 m to 40 m, and from 5 m to 30 m, more preferably from 7 m to 50 m, from 7 m to 40 m, and from 7 m to 30 m, and even more preferably from 9 m to 50 m, from 9 m to 40 m, and from 9 m to 30 m, for example, in a case in which a tube having an equivalent diameter of about from 6 mm to 10 mm is used.

It is required to execute the reaction at a high temperature in order to efficiently perform the method of the present invention, and thus it is required to raise the temperature, and the length of the tube is generally required to be 5 m or more although it is required to take a balance with the flow rate into consideration in a case in which a tube having an equivalent diameter of about from 1 mm to 6 mm or 6 mm to 10 mm is used.

The flow rate in the flow reactor of the present invention, preferably the tubular flow reactor, is usually 0.5 m/min or more, preferably 1.0 m/min or more, more preferably 5 m/min or more, even more preferably from 5 m/min to 50 m/min, and particularly preferably from 10 m/min to 40 m/min or so although it is dependent on the equivalent diameter of the tube.

(Reaction Apparatus)

The reaction apparatus of the present invention is illustrated in FIGS. 1 to 5 for description, but the reaction apparatus of the present invention is not limited thereto.

FIG. 1 represents the most typical example of the reaction apparatus of the present invention.

Three kinds of raw material compounds are supplied through the raw material inlets 1 to 3, respectively. In the example of FIGS. 1 to 5, the reaction apparatus is illustrated in such a manner that each of the three kinds of the raw material compounds is supplied through a separate inlet, but it is not necessarily required to supply the three kinds separately and it is also possible to supply a mixture prepared by mixing two kinds among these in advance.

In the example of FIG. 1, a malonic acid diester, a carboxylic acid compound, and a chlorous acid compound are supplied to the mixer 11 through the inlets 1 to 3, respectively, and these are then mixed. The order of mixing is not particularly limited, and it is possible that the carboxylic acid compound and the chlorous acid compound are mixed and subsequently the malonic acid diester is mixed with this mixture, or it is also possible that the malonic acid diester and the carboxylic acid compound are mixed and subsequently the chlorous acid compound is mixed with this mixture. As the more preferred aspect, it is also possible that the malonic acid diester and the carboxylic acid compound are mixed in advance, and this mixture is supplied through the inlet 1 and an aqueous solution of the chlorous acid compound is supplied through the inlet 2 and mixed together. In this case, the inlet 3 is not used.

The malonic acid diester, the carboxylic acid compound, and the chlorous acid compound can be mixed at the molar ratio described above. For example, the molar ratio of these can be selected in the range of 1 mol:0.01 to 50 mol:1 to 15 mol.

This mixing process is the same in FIGS. 2 to 5 below.

The mixture mixed in the mixer 11 is supplied to the tubular flow reactor 12 and subjected to the reaction. The reaction mixture after the reaction is recovered through the outlet 4.

The tubular flow reactor 12 can be conceptually separated into the temperature rising part and the reaction part. As the temperature rising part, the length of the tube is required to be 2 m or more, preferably 3 m or more, and more preferably 5 m or more although it is dependent on the equivalent diameter of the tube or flow rate. Meanwhile, the temperature rising part would not be necessary in a case in which the temperature of the raw material compounds is raised enough before the raw material compounds are introduced into the tubular flow reactor. More specifically, the length of the temperature rising part required for temperature rising is, for example, about from 2 m to 10 m, preferably from 3 m to 7 m, and more preferably from 3 m to 5 m or so. As the reaction part, the length of the tube is required to be 1 m or more, 2 m or more, 3 m or more, 5 m or more, or 10 m or more although it is dependent on the equivalent diameter of the tube or flow rate. More specifically, the length of the reaction part required for reaction is, for example, about from 3 m to 20 m, from 3 m to 15 m, and from 3 m to 10 m, or about from 4 m to 20 m, from 4 m to 15 m, and from 4 m to 10 m or so.

The equivalent diameter of the tube of the tubular flow reactor 12 is from 0.5 mm to 50 mm, from 0.5 mm to 30 mm, and from 0.5 mm to 10 mm, and preferably from 1 mm to 50 mm, from 1 mm to 30 mm, from 1 mm to 10 mm, and from 3 mm to 10 mm or so.

The length of the tube of the tubular flow reactor 12 is in the range of 5 m or more, preferably from 5 m to 50 m, from 5 m to 30 m, and from 5 m to 20 m, preferably from 7 m to 50 m, from 7 m to 30 m, from 7 m to 20 m, and more preferably from 9 m to 50 m, from 9 m to 30 m, and from 9 m to 20 m.

The flow rate of the tubular flow reactor 12 is preferably 5 m/min or more, more preferably from 5 m/min to 50 m/min, and even more preferably from 10 m/min to 40 m/min or so.

The residence time in the tubular flow reactor 12 is usually 10 seconds or longer, preferably from 10 seconds to 200 seconds, from 10 seconds to 150 seconds, and from 10 seconds 120 seconds, more preferably from 15 seconds to 200 seconds, from 15 seconds to 150 seconds, and from 15 seconds to 120 seconds or so although it is dependent on flow rate or the size of the equivalent diameter.

The tubular flow reactor 12 is provided with a temperature control unit (for example, a bath to control the temperature), and the temperature of the temperature control unit (for example, a bath to control the temperature) is preferably from 60° C. to 200° C., from 80° C. to 200° C., and from 90° C. to 200° C., more preferably from 80° C. to 150° C. and from 90° C. to 150° C., and even more preferably from 100° C. to 150° C. and from 100° C. to 140° C. or so.

The temperature of the mixture in the tubular flow reactor 12 is, for example, from 60° C. to 250° C., from 80° C. to 250° C., and from 90° C. to 250° C., preferably from 60° C. to 200° C., from 80° C. to 200° C. and from 90° C. to 200° C., even more preferably from 80° C. to 170° C., and from 90° C. to 170° C., even more preferably from 80° C. to 160° C. and from 90° C. to 160° C., even more preferably from 80° C. to 150° C., from 90° C. to 150° C., and from 100° C. to 150° C., and particularly preferably from 120° C. to 150° C. and from 130° C. to 150° C., but it is not limited thereto. As a preferred aspect of the temperature control, a method can be exemplified in which the temperature of the mixture in the tubular flow reactor 12 is measured and the temperature of the temperature control unit is adjusted so that the temperature of the mixture becomes the temperature described above. In addition, a method can be also exemplified in which the temperature of the reaction mixture is measured in the vicinity of the outlet of the tubular flow reactor 12 and the temperature of the temperature control unit is adjusted so that the temperature of the mixture becomes the temperature described above.

In addition, the average pressure in the tubular flow reactor 12 of the present invention is, for example, in the range of from 0.03 MPa to 1.0 MPa and from 0.03 MPa to 0.9 MPa, preferably from 0.05 MPa to 0.8 MPa, from 0.05 MPa to 0.7 MPa, from 0.04 MPa to 1.0 MPa, from 0.04 MPa to 0.9 MPa, and more preferably from 0.09 MPa to 0.3 MPa, from 0.1 MPa to 0.3 MPa, from 0.04 MPa to 0.8 MPa, and from 0.04 MPa to 0.7 MPa, but it is not limited thereto.

Figure 2:
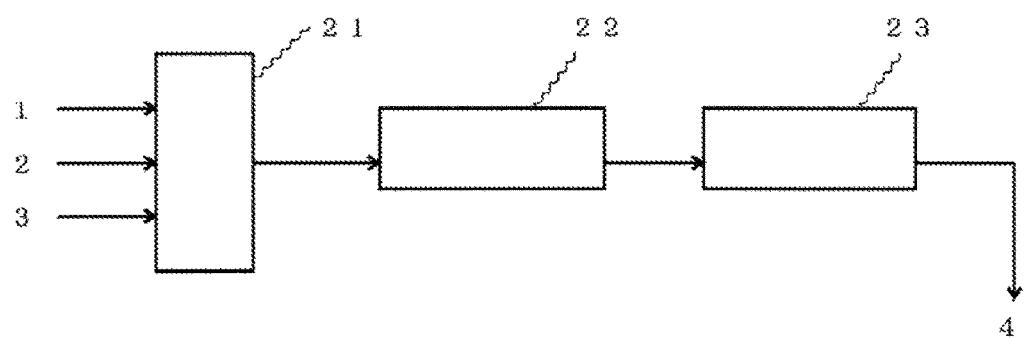
FIG. 2 schematically illustrates the outline of the reaction apparatus of the present invention in the case of using two flow reactors 22 and 23.

FIG. 1 represents an example of a case in which there is one flow reactor, but it is also possible to separately operate using two or more flow reactors. FIG. 2 represents an example of the case of using two flow reactors 22 and 23.

The mixture of the raw material compounds mixed in the mixer 21 is supplied to the first flow reactor 22 and subsequently supplied to the flow reactor 23 in the same manner as the case of FIG. 1. The temperature of the mixture is raised to the reaction temperature in the first flow reactor 22. Subsequently, the temperature-raised mixture is supplied to the subsequent flow reactor 23 and subjected to the reaction, and the reaction mixture can be recovered through the outlet 4.

The first flow reactor 22 is a flow reactor for the temperature rising part and is preferably a tubular flow reactor, and the length of the tube is required to be 2 m or more, preferably 3 m or more, and more preferably 5 m or more although it is dependent on the equivalent diameter of the tube or flow rate. More specifically, the length is, for example, about from 2 m to 10 m, preferably from 3 m to 7 m, and more preferably from 3 m to 5 m or so.

The subsequent flow reactor 23 is a flow reactor for the reaction part and is preferably a tubular flow reactor, and the length of the tube is required to be 3 m or more, 5 m or more, or 10 m or more although it is dependent on the equivalent diameter of the tube or flow rate. More specifically, the length is, for example, about from 3 m to 20 m, from 3 m to 15 m, and from 3 m to 10 m or about from 4 m to 20 m, from 4 m to 15 m, and from 4 m to 10 m or so.

The reaction conditions such as the temperature condition are the same as the case of FIG. 1 above.

As a variation of the reaction path illustrated in FIG. 2, it is possible that the order of the mixer 21 and the first flow reactor 22 are switched in the reaction path. In other words, it is possible that the temperature of each of the raw material compounds is raised by the flow reactor 22 prior to mixing the raw material compounds, subsequently the temperature-raised raw material compounds are mixed, and the mixture is supplied to the flow reactor 23 in order to subject the temperature-raised raw material compounds to the reaction. However, it is not a preferred aspect since not only the apparatus is complicated but also the chlorous acid compound is singly heated.

Figure 3:
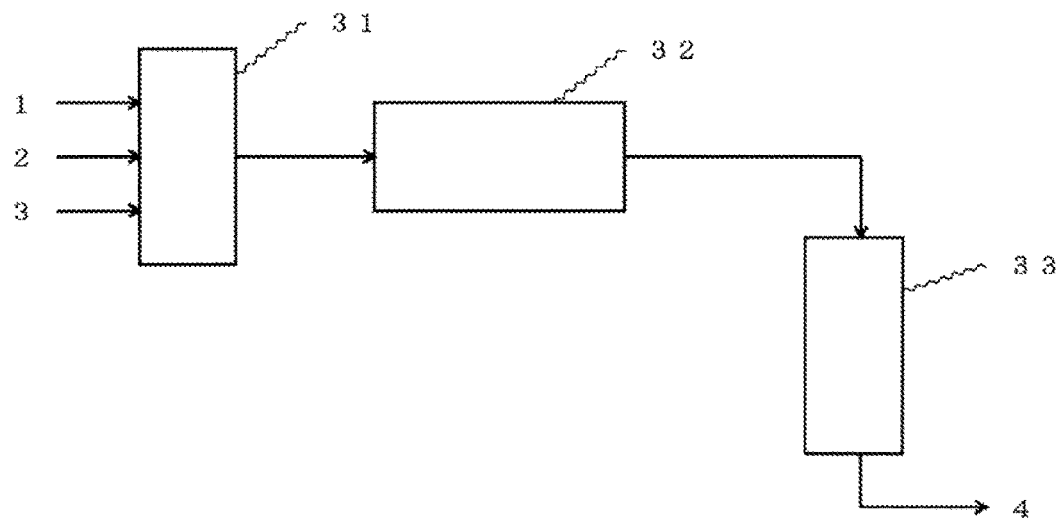
FIG. 3 schematically illustrates the outline of the reaction apparatus of the present invention in a case in which the apparatus illustrated in FIG. 1 is further provided with a flow reactor 33 for an aging process.

FIG. 3 represents an example of a case in which the apparatus illustrated in FIG. 1 is further provided with a flow reactor 33 for an aging process. The operations in a mixer 31 and a flow reactor 32 are the same as the case of FIG. 1 above until the reaction mixture is supplied to the flow reactor 33 for the aging process.

It is presumed that the reaction of the malonic acid diester with a chlorite contains two or more steps, and it is required to heat to a high temperature for processing the first step of the reaction but it is not necessarily required to heat for the reaction of the last step. It can be considered that this is because the reaction of the first step is an exothermic reaction, and thus it is possible to maintain the reaction temperature in the reaction mixture by using the heat of reaction even without external heating after this exothermic reaction has proceeded. Consequently, it is considered that the thermal efficiency can become favorable and the conversion ratio can be further improved by retaining the reaction mixture at a low temperature after the reaction at a high temperature is completed. This process of conducting the retention at a low temperature is the aging process.

The flow reactor 33 is preferably a tubular flow reactor.

The equivalent diameter of the tube of the tubular flow reactor 33 may be the same as the equivalent diameter of the tube of the tubular flow reactor 32 but is preferably smaller than that, and it may be about half of the equivalent diameter of the tube of the tubular flow reactor 32.

The length of the tube of the tubular flow reactor 33 is preferably from 3 m to 30 m, from 3 m to 15 m, and from 3 m to 10 m or so.

The flow rate of the tubular flow reactor 33 is almost the same as the flow rate of the tubular flow reactor 32.

The tubular flow reactor 33 does not particularly require a temperature control unit (for example, a bath to control the temperature) but is preferably provided with a temperature control unit for cooling. The temperature control unit is preferably a bath and more preferably a water-cooling bath.

The mode of bath may be any suitable modes in the present specification, and for example, may be a "retention type", a "fluidized type (circulation type)", additionally, an "open type", or a "closed type". In the present specification, the "water cooling" means a cooling method, for example, a cooling method using a heat medium such as a liquid consisting of a single component such as water and an alcohol as the antifreezing fluid or a mixed liquid such as an aqueous solution of an alcohol, saline water, and an aqueous solution of calcium chloride as the antifreezing fluid, and here, examples of the alcohol include ethylene glycol and propylene glycol.

Figure 4:
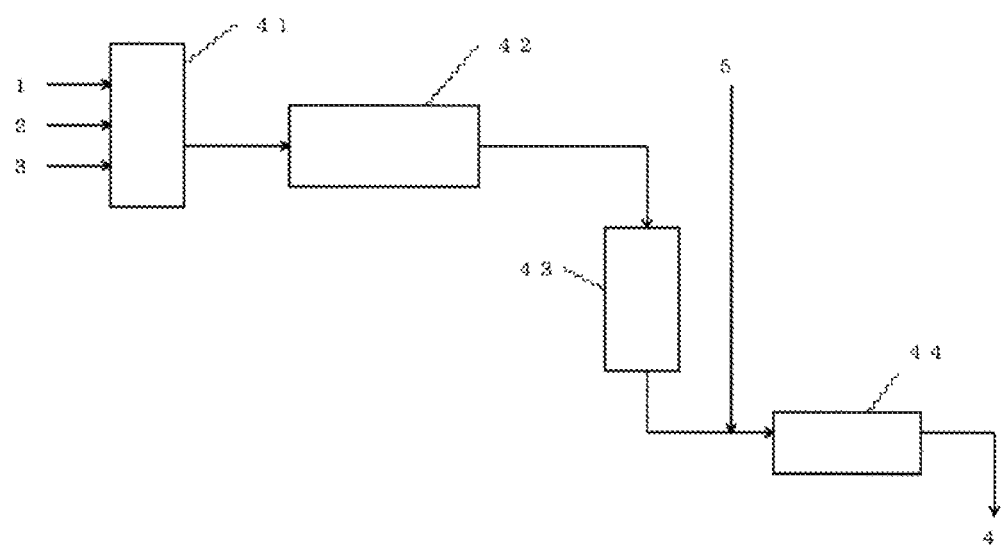
FIG. 4 schematically illustrates the outline of the reaction apparatus of the present invention in a case in which the apparatus illustrated in FIG. 3 is further provided with a flow reactor 44 for a quenching process.

FIG. 4 represents an example of a case in which the apparatus illustrated in FIG. 3 is further provided with a flow reactor 44 for a quenching process. The operations in a mixer 41, a flow reactor 42, and a flow reactor 43 are the same as the case of FIG. 3 above until the reaction mixture is supplied to the flow reactor 44 for the quenching process.

The desired reaction is completed by the apparatus illustrated in FIG. 3, but the reaction mixture may contain the unreacted raw material compounds, an explosive substance of a byproduct, and the like. This quenching process is a process to safely treat these substances.

In other words, this quenching process is a process to decompose the unreacted chlorite and chlorine dioxide of a byproduct. The chemical formulas of the decomposition reaction presumed in the case of using an aqueous solution of $Na_2SO_3$ and NaOH as the quench liquid are presented below.

$$NaClO_2 + 2Na_2SO_3 \rightarrow 2Na_2SO_4 + NaCl$$

$$ClO_2 + NaOH + 3/2Na_2SO_3 \rightarrow 3/2Na_2SO_4 + NaCl + 1/2H_2O + 1/2O_2$$

Decomposing the unreacted chlorite and produced chlorine dioxide in the reaction mixture in this manner enables performing the separation and purification treatment of the reaction mixture more easier as well as executing waste water treatment, and thus it is possible to decrease the leakage of waste water to the environment.

The flow reactor 44 is preferably a tubular flow reactor.

The quench liquid is not particularly limited as long as it contains a substance capable of decomposing the unreacted chlorite and chlorine dioxide of a byproduct in the reaction mixture, and examples of the preferred quench liquid may include an aqueous solution of a sulfite and/or an alkali metal hydroxide.

The quench liquid is supplied to the reactor tube, for example, by a T-shaped tube, a Y-shaped tube and the like and mixed. The T-shaped tube, Y-shaped tube, and the like for mixing is preferably provided in front of the tubular flow reactor 44, but it is not limited thereto.

The equivalent diameter of the tube of the tubular flow reactor 44 may be the same as the equivalent diameter of the tube of the tubular flow reactor 42 but is preferably smaller than that, and it may be about half of the equivalent diameter of the tube of the tubular flow reactor 42.

The length of the tube of the tubular flow reactor 44 is preferably from 3 m to 30 m, from 3 m to 15 m, and from 3 m to 10 m or so.

The flow rate of the tubular flow reactor 44 is almost the same as the flow rate of the tubular flow reactor 42.

The tubular flow reactor 44 does not particularly require a temperature control unit (for example, a bath to control the temperature) but is preferably provided with a temperature control unit for cooling. The temperature control unit is preferably a bath and more preferably a water-cooling bath.

Figure 5:
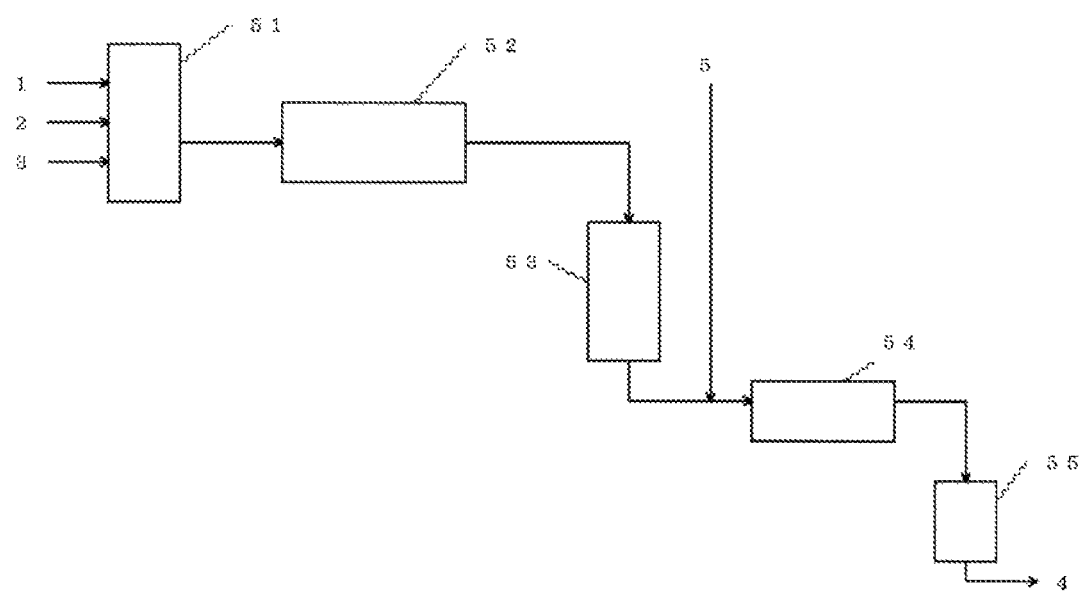
FIG. 5 schematically illustrates the outline of the reaction apparatus of the present invention in a case in which the apparatus illustrated in FIG. 4 is further provided with a separation and purification device 55 for a separation process of the desired product.

FIG. 5 represents an example of a case in which the apparatus illustrated in FIG. 4 is further provided with a separation and purification device 55 for a separation process of the desired product. The operations in a mixer 51, a flow reactor 52, a flow reactor 53, and a flow reactor 54 for the quenching process are the same as the case of FIG. 4 above until the reaction mixture is supplied to the separation and purification device 55.

As a treatment with the separation and purification device 55, a batch type reactor may be used or a vessel type flow reactor can also be used.

The product is obtained in the form of a hydrate of ketomalonic acid diester represented by a general formula (3) when the method of the present invention in which a corresponding ketomalonic acid diester or a hydrate thereof is produced using a malonic acid diester, a carboxylic acid compound, and a chlorous acid compound as the raw material compounds is performed in the presence of water medium, while the product is obtained in the form of a ketomalonic acid diester represented by a general formula (2) when performed under a nonaqueous condition.

A preferred aspect of the method of the present invention is the reaction in the presence of water medium, and thus the product is obtained in the form of a hydrate of ketomalonic acid diester represented by the general formula (3). In order to convert the hydrate of ketomalonic acid diester obtained to a ketomalonic acid diester represented by the general formula (2), the hydrate of ketomalonic acid diester is subjected to, for example, a dehydration treatment such as the azeotropic dehydration with toluene so as to dehydrate the hydrate, whereby a ketomalonic acid diester represented by the general formula (2) can be easily obtained. In other words, the reaction of the present invention is preferably performed in the presence of water medium since it is possible to change the form of the isolated product to the desired form which is either of the form of a ketomalonic acid diester represented by the general formula (2) or the form of a hydrate of ketomalonic acid diester represented by the general formula (3) by appropriately selecting the reaction solvent and the method of the treatment after the reaction in the method of the present invention.

Meanwhile, examples of the method of separating a hydrate of ketomalonic acid diester represented by the general formula (3) from the reaction mixture may include a method in which an extraction treatment is performed using an extraction solvent such as ethyl acetate.

(Continuous Reaction Apparatus)

The continuous reaction apparatus of the present invention is a continuous reaction apparatus which includes a mixer of the raw material compounds and a flow reactor, preferably a tubular flow reactor for the continuous reaction, and it is firstly characterized in that the continuous reaction apparatus is for the production of a corresponding ketomalonic acid diester or a hydrate thereof using a malonic acid diester, a carboxylic acid compound, and a chlorous acid compound as the raw material compounds.

In addition, the continuous reaction apparatus of the present invention is secondly characterized in that the equivalent diameter of the tube of the flow reactor, preferably the tubular flow reactor is relatively great to be from 0.5 mm to 50 mm in order to efficiently produce a ketomalonic acid diester or a hydrate thereof.

Moreover, the continuous reaction apparatus of the present invention is thirdly characterized in that the continuous reaction apparatus is provided with a temperature rising part for raising the temperature of the mixture of raw materials in a short period of time. The temperature rising part is a portion of the flow reactor, and the temperature rising part and the reaction part may be in one flow reactor, or a flow reactor for the temperature rising part and a flow reactor for the reaction part may be sequentially or separately disposed.

Next, methods of producing compounds according to the present invention will be specifically described with reference to Examples, but the present invention is not limited to these Examples in any way.

The analytical method by gas chromatography (GC) and the method of measuring the flow rate in the following Examples were adopted by the following methods.

(Analytical Method by Gas Chromatography (GC))

With regard to the analytical method by GC, the following documents can be referred, as desired.

(a): "Shin Jikken Kagaku Koza 9, Bunsekikagaku II (A New Course in Experimental Chemistry 9, Analytical Chemistry II)", edited by The Chemical Society of Japan, pp. 60 to 86 (1977), published by IIZUMI Shingo, Maruzen Co., Ltd. (for example, it is possible to refer to pp. 66 of this document with respect to liquids for a stationary phase to be usable for a column.)

(b): "Jikken Kagaku Koza 20-1, Bunsekikagaku (A Course in Experimental Chemistry 20-1, Analytical Chemistry)", edited by The Chemical Society of Japan, 5th edition, pp. 121 to 129 (2007), published by MURATA Seishiro, Maruzen Co., Ltd. (for example, it is possible to refer to pp. 124 to 125, with respect to the specific usage of hollow capillary separation columns.)

(Conversion Ratio)

The conversion ratio was calculated by the following method.

Calculation Method of Conversion Ratio:

The conversion ratio was calculated using the value obtained by subtracting the peak of the solvent from the value of area percentage obtained by the gas chromatography (GC) analysis.

GC Analysis Conditions:

Instrument: GC-2010 (manufactured by Shimadzu Corporation)

Column: DB-1 (Aglient J & W)

Temperature-rising condition: 80° C. (0 min)→10° C./min→200° C. (2 min)

Injection temperature: 300° C.

Detector temperature: 320° C.

Detection method: FID

Method of Preparing Samples for Analysis:

A small amount of reaction mixture obtained by the method of the present invention was sampled and an appropriate amount of ethyl acetate was added thereto. The sample thus obtained was thoroughly stirred and allowed to stand still. The organic layer of the upper layer was separated and used as the analytical sample for gas chromatography.

(Method of Measuring Flow Rate)

The flow rate was calculated by the following method since it is difficult to directly measure the actual flow rate.

The weight of each raw material before and after the reaction was weighed by a weighing scale such as a balance. The flow rate ($m^3$/min) was calculated by dividing the weight difference (kg) therebetween by density (kg/$m^3$) of each raw material to convert to volume difference ($m^3$), and further dividing it by the operation time (min). The result obtained by dividing the flow rate thus obtained by the average cross-sectional area ($m^2$) of the reactor tube was adopted as the mean flow rate (m/min). However, since the reaction mixture was in a gas-liquid mixed state and the actual flow rate fluctuates, it was difficult to obtain a stable measurement value. Therefore, the calculated mean flow rate is for reference and does not necessarily correspond to the actual flow rate.

(Method of Measuring Pressure)

The pressure was measured by the following method.

The average value of the pressure in the steady state (constant reaction stage) was calculated from the data group obtained by the diaphragm type pressure gauge equipped to the reactor.

Pressure gauge: diaphragm type pressure gauge PK-1 and/or diaphragm type digital pressure gauge DDIT (both of them are manufactured by DAIICHI KEIKI SEISAKUSHO CO., LTD.).

EXAMPLE 1

(Method Using a Microreactor)

Two microreactors (mixer helix type manufactured by YMC CO., LTD.) were prepared, and the outlet of the first microreactor was connected to one of the inlets of the second microreactor using a tube. A Teflon (registered trademark) tube with a diameter of 1.0 mm and a length of 9 m was connected to the outlet of the second microreactor so as to use the Teflon (registered trademark) tube as the reactor tube. The 9 m Teflon (registered trademark) tube was immersed in a silicone oil bath so as to be heatable.

The first microreactor was heated to 80° C., the silicone oil bath was heated to 130° C., a 25% aqueous solution of sodium chlorite and acetic acid were respectively supplied to the first microreactor through the two inlets using a syringe pump, and diethyl malonate without a solvent was supplied through the other inlet of the second microreactor using a syringe pump.

The supply ratio was that diethyl malonate:acetic acid: 25% aqueous solution of sodium chlorite was set to 1:3:3 in a volume ratio.

The flow rate in the Teflon (registered trademark) tube was 0.74 m/min. The reaction mixture discharged through the outlet of the Teflon (registered trademark) tube was analyzed by gas chromatography and the conversion ratio of diethyl malonate was 63.70% as a result.

EXAMPLE 2

The apparatus used in Example 1 was used, both of the first and second microreactors were not heated but left at room temperature, the silicone oil bath was heated to 95° C., and in the same manner as in Example 1, a 25% aqueous solution of sodium chlorite and acetic acid were respectively supplied to the first microreactor through the two inlets using a syringe pump and diethyl malonate without a solvent was supplied through the other inlet of the second microreactor using a syringe pump.

The supply ratio was that diethyl malonate:acetic acid: 25% sodium chlorite aqueous solution was set to 1:1:10 in a volume ratio.

The flow rate in the Teflon (registered trademark) tube was 1.27 m/min. The reaction mixture discharged through the outlet of the Teflon (registered trademark) tube was analyzed by gas chromatography, and the conversion ratio of diethyl malonate was 86.50% as a result.

COMPARATIVE EXAMPLE 1

Two microreactors (mixer helix type manufactured by YMC CO., LTD.) were prepared, and the outlet of the first microreactor was connected to one of the inlets of the second microreactor using a tube. The Teflon (registered trademark) tube connected in Example 1 was not used.

The first and second microreactors were heated to 80° C., a 25% aqueous solution of sodium chlorite and acetic acid were respectively supplied through the two inlets of the first microreactor using a syringe pump, and diethyl malonate without a solvent was supplied through the other inlet of the second microreactor using a syringe pump.

The supply ratio was that diethyl malonate:acetic acid: 25% sodium chlorite aqueous solution was set to 1:1:1 in a volume ratio. The flow rate was 0.32 m/min.

The reaction mixture discharged through the outlet of the second microreactor was analyzed by gas chromatography and the conversion ratio of diethyl malonate was merely 0.29% as a result.

COMPARATIVE EXAMPLE 2

The same operation as in Comparative Example 1 was performed except that the second microreactor was heated to 120° C. and the flow rate was 0.96 m/min and the conversion ratio of diethyl malonate was merely 1.42% as a result.

As can be seen from the results of Comparative Examples 1 and 2 as well, the reaction did not proceed when only the microreactors were used. On the contrary, it has been found out that there is a possibility that the reaction proceeds when a 9 m reactor tube is used to raise the temperature.

In addition, it has been also demonstrated that an excessive amount of sodium chlorite is desirable as a result of extensive investigations on the conditions.

EXAMPLES 3 TO 6

In order to conduct a reaction by the use of only one microreactor, a mixture of acetic acid and diethyl malonate was prepared in advance at a weight ratio of diethyl malonate:acetic acid of 5:1 and this mixture was supplied through one inlet. A 25% aqueous solution of sodium chlorite was supplied through the other inlet of the microreactor. A tube with a diameter of 1 mm and a length of 9 m was connected to the outlet of the microreactor and managed so as to be heated by a silicone oil bath in the same manner as in Example 1.

The conversion ratio was measured for each of the cases in which the molar ratio of sodium chlorite to diethyl malonate, the flow rate, the temperature of the microreactor, and the bath temperature were changed.

The results are presented in the following Table 1.

TABLE 1

| Example No. | Concentration of sodium chlorite | Molar ratio | Temperature of the microreactor | Mean flow rate (m/min) | Diameter of the reactor tube | Length of the reactor tube | Bath temperature | Conversion ratio (%) |
| --- | --- | --- | --- | --- | --- | --- | --- | --- |
| 3 | 25% | 3 | 80° C. | 1.27 | 1 mm | 9 m | 80° C. | 96.98% |
| 4 | 25% | 2.4 | 80° C. | 1.06 | 1 mm | 9 m | 80° C. | 87.72% |
| 5 | 25% | 3 | 60° C. | 1.27 | 1 mm | 9 m | 60° C. | 89.67% |
| 6 | 25% | 2.7 | 80° C. | 1.17 | 1 mm | 9 m | 80° C. | 93.16% |

From these results, it has been found out that a practical conversion ratio can be achieved by using a reactor tube.

EXAMPLE 7

A commercially available 25% aqueous solution of sodium chlorite was used in Examples 1 to 6, however, it was investigated whether the reaction proceeded or not even when using a 15% aqueous solution of sodium chlorite as a diluted solution of the above in the present Example.

The same apparatus as in Example 3 was used, the temperature of the microreactor was set to 20° C., the bath temperature was set to 80° C., the volume ratio of diethyl malonate:acetic acid:15% aqueous solution of sodium chlorite was set to 1:0.2:6.7, and the reaction was conducted in the same manner as in Example 3. The mean flow rate was 3.02 m/min. The conversion ratio was 99.46%, and it was possible to obtain diethyl ketomalonate of the desired product from the reaction mixture at a yield of 85.0%.

EXAMPLE 8

The reaction was conducted in the same manner as in Example 7 except that the microreactor was left at room temperature. The conversion ratio was 92.89%.

EXAMPLE 9

From the results above, it has been found out that the reaction does not proceed in the microreactor but the microreactor simply functions as a mixer, and thus mixing was performed by a T-shaped tube instead of the microreactor in the present Example. The pump used was also changed from the syringe pump to a plunger pump for HPLC. In addition, the reactor tube was also extended to 20 m and a 10 m tube was further attached to the end thereof for cooling (standing to cool). The bath temperature for the reactor tube was set to 80° C., sodium chlorite and diethyl malonate was supplied to the T-shaped tube at a molar ratio of sodium chlorite to diethyl malonate of 2.0. The mean flow rate was 12.01 m/min. The conversion ratio was 97.36%.

EXAMPLE 10

In order to confirm whether it was possible to conduct the reaction in a plurality of reactor tubes, the mixed raw materials was split into two lines by the use of T-shaped tube and the reaction was conducted in the same manner as in Example 9. As a result, the conversion ratio was 96.34%, respectively.

This result indicates that it is possible to branch the reactor tube into a plurality of reactor tubes and to simultaneously conduct the reaction in each of the reactor tubes according to the method of the present invention.

EXAMPLE 11

The reaction was conducted in the same manner as in Example 9 except that the length of the reactor tube was set to 10 m, the bath temperature for the reactor tube was set to 110° C., and a 10% aqueous solution of sodium chlorite was used. The mean flow rate was 5.01 m/min. The conversion ratio was 97.29%. It was possible to perform a safe operation although small scale explosions seemed to have occurred in the reactor tube but there was no problem caused by it.

EXAMPLE 12

The reaction was conducted in the same manner as in Example 11 except that the 10 m cooling tube at the end of the reactor tube was divided into 5 m and 5 m and one 5 m portion was subjected to water cooling but not standing to cool. The conversion ratio was 99.13%. A number of small scale explosions were observed as in Example 11.

As described above, it has been found out that the reaction of the present invention does not proceed in the reaction system such as a microreactor which only has a short flow path, however, a practical conversion ratio is achieved by providing the induction period (providing temperature rising part) until the reaction is proceeded in a long reactor tube. At the same time, it has been also found out that explosions occur although which explosions are a small scale ones when the bath temperature is high.

Hence, a reaction using a metallic tubular flow reactor which is excellent in pressure resistance was attempted.

Figure 6:
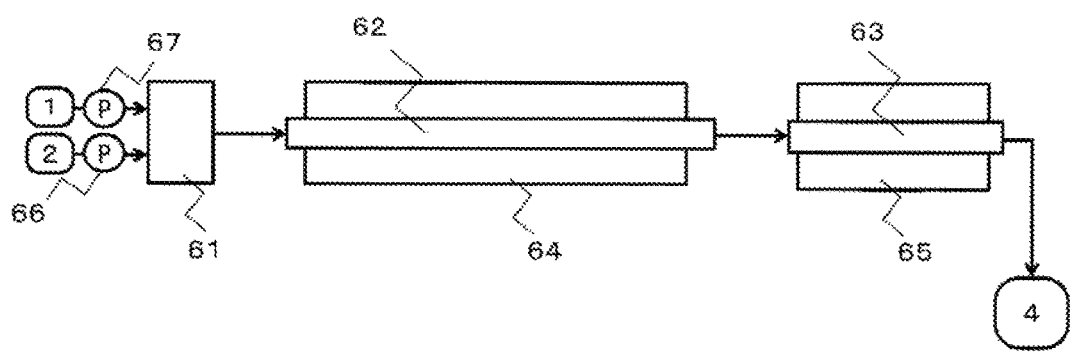
FIG. 6 schematically illustrates the outline of the reaction apparatus of the present invention used in Example 13 and the like. The mixture of raw material compounds is introduced into a tubular flow reactor 62 having a bath 64 and subsequently introduced into a tubular flow reactor 63 having a water bath 65 to be aged.

The outline of the apparatus is illustrated in FIG. 6. A container 1 contains an aqueous solution of sodium chlorite of a raw material, and a container 2 contains a mixture of diethyl malonate and acetic acid of raw materials at a weight ratio of 5:1 (a molar ratio of 1:0.5). These raw materials are respectively supplied via pumps 67 and 66. Each of the raw materials thus supplied is mixed by a mixer 61. The mixture is introduced into a tubular flow reactor 62 made of a titanium tube with an inner diameter of 3.15 mm. The tubular flow reactor 62 is housed in a bath 64. The reaction mixture discharged from the tubular flow reactor 62 is then introduced into a tubular flow reactor 63 also made of a titanium tube with an inner diameter of 3.15 mm. The tubular flow reactor 63 is housed in a water bath 65 for water cooling. The temperature of the heat medium (coolant) for water cooling was set to 25° C. unless otherwise stated when performing water cooling in Examples of the present specification. The reaction mixture discharged from the tubular flow reactor 63 passes through the pipe to be accumulated in a container 4. Both tubes of the tubular flow reactor 62 and the tubular flow reactor 63 are wound into a coil shape.

The following production experiments were conducted using this reaction apparatus.

The results of the experiments are presented in each of the following Tables. In each of Tables, the "molar ratio" represents the molar ratio of sodium chlorite to diethyl malonate and the "mean flow rate" represents the average value of flow rate in the entire tube and the unit thereof is m/min. The "length of the reactor tube" represents the length of tube of the tubular flow reactor 62, the "heat transfer time (seconds)" represents the time (seconds) of residence in the tubular flow reactor 62, and the "length of the cooling tube" represents the length of the tube of the tubular flow reactor 63.

EXAMPLES 13 TO 15

The investigation was conducted on the concentration of the aqueous solution of sodium chlorite used as a raw material. The reaction was conducted using aqueous solutions of sodium chlorite having a concentration of 25%, 15%, and 10%, respectively.

The results are presented in the following Table 2.

TABLE 2

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 13 | 25% | 2.03 | 23.42 | 3.15 mm | 15 m | 112° C. | 0.4 | 38 | 3.15 mm | 5 m | Water cooling | 76.42 |
| 14 | 15% | 2.19 | 35.42 | 3.15 mm | 15 m | 112° C. | 0.4 | 25.4 | 3.15 mm | 5 m | Water cooling | 95.43 |
| 15 | 10% | 2.07 | 31.81 | 3.15 mm | 15 m | 112° C. | 0.28 | 28.3 | 3.15 mm | 5 m | Water cooling | 96.35 |

As a result, it is indicated that a practical conversion ratio is achieved at any of the concentrations of the aqueous solutions of sodium chlorite.

EXAMPLES 16 TO 21

Next, the influence of the bath temperature of the tubular flow reactor 62 was investigated.

The bath temperature was changed to from 82° C. to 112° C. The results are presented in the following Table 3.

TABLE 3

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 16 | 10% | 2.00 | 37.46 | 3.15 mm | 10 m | 132° C. | 0.532 | 16.0 | 3.15 mm | 5 m | Water cooling | 84.23 |
| 17 | 10% | 2.24 | 37.79 | 3.15 mm | 10 m | 127° C. | 0.418 | 15.9 | 3.15 mm | 5 m | Water cooling | 97.78 |
| 18 | 10% | 2.11 | 30.74 | 3.15 mm | 10 m | 122° C. | 0.352 | 19.5 | 3.15 mm | 5 m | Water cooling | 97.80 |
| 19 | 10% | 2.03 | 30.46 | 3.15 mm | 15 m | 112° C. | 0.26 | 29.5 | 3.15 mm | 5 m | Water cooling | 98.07 |
| 20 | 10% | 2.03 | 31.69 | 3.15 mm | 15 m | 104° C. | 0.15 | 28.4 | 3.15 mm | 5 m | Water cooling | 83.53 |
| 21 | 10% | 1.96 | 32.44 | 3.15 mm | 15 m | 82° C. | 0.06 | 27.7 | 3.15 mm | 5 m | Water cooling | 5.53 |

As a result, the reaction proceeded in all examples although the conversion ratio was low when the bath temperature is 80° C. or higher. Hence, it has been found out it is sufficient to have a bath temperature of 80° C. or higher and preferably 100° C. or higher.

In addition, the reaction at a high temperature in a short time was investigated by increasing the flow rate and setting the length of the tube of the tubular flow reactor 62 to 10 m in Examples 16 to 18.

EXAMPLES 22 TO 28

Next, the influence of the flow rate was investigated.

The investigation was conducted in a range of from 7 m/min to 40 m/min. The results are presented in the following Table 4.

TABLE 4

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 22 | 10% | 2.17 | 38.04 | 3.15 mm | 15 m | 112° C. | 0.33 | 23.7 | 3.15 m | 5 m | Water cooling | 98.74 |
| 23 | 10% | 2.08 | 34.04 | 3.15 mm | 15 m | 112° C. | 0.30 | 26.4 | 3.15 m | 5 m | Water cooling | 95.56 |
| 24 | 10% | 2.15 | 28.03 | 3.15 mm | 15 m | 112° C. | 0.23 | 32.1 | 3.15 m | 5 m | Water cooling | 95.24 |
| 25 | 10% | 2.21 | 20.47 | 3.15 mm | 15 m | 112° C. | 0.16 | 44.0 | 3.15 m | 5 m | Water cooling | 96.07 |
| 26 | 10% | 2.24 | 17.06 | 3.15 mm | 15 m | 112° C. | 0.11 | 52.8 | 3.15 m | 5 m | Water cooling | 98.57 |
| 27 | 10% | 2.60 | 10.63 | 3.15 mm | 15 m | 112° C. | 0.08 | 84.7 | 3.15 m | 5 m | Water cooling | 91.35 |
| 28 | 10% | 1.66 | 7.56 | 3.15 mm | 15 m | 112° C. | 0.07 | 119.1 | 3.15 m | 5 m | Water cooling | 96.30 |

As a result, the conversion ratio was not affected so much by a change in the flow rate in a case in which the bath temperature was 112° C.

EXAMPLES 29 TO 35

Next, the pressure in the tube was investigated in the experiments which were conducted using the tubular flow reactor 62 having a length of the tube of 10 m. A T-shaped connector was used instead of the mixer of the mixer 61 in Example 34. However, it has already been confirmed that the result is little affected by this change.

The results are presented in the following Table 5.

TABLE 5

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 29 | 10% | 2.21 | 11.85 | 3.15 mm | 10 m | 112° C. | 0.073 | 50.6 | 3.15 mm | 5 m | Water cooling | 76.30 |
| 30 | 10% | 2.02 | 21.42 | 3.15 mm | 10 m | 112° C. | 0.169 | 28.0 | 3.15 mm | 5 m | Water cooling | 92.72 |
| 31 | 10% | 2.18 | 34.09 | 3.15 mm | 10 m | 112° C. | 0.280 | 17.6 | 3.15 mm | 5 m | Water cooling | 93.31 |
| 32 | 10% | 2.21 | 30.43 | 3.15 mm | 10 m | 112° C. | 0.310 | 19.7 | 3.15 mm | 5 m | Water cooling | 98.19 |
| 33 | 10% | 2.02 | 30.86 | 3.15 mm | 10 m | 112° C. | 0.391 | 19.4 | 3.15 mm | 5 m | Water cooling | 98.93 |
| 34 | 10% | 2.09 | 28.93 | 3.15 mm | 10 m | 112° C. | 0.540 | 20.7 | 3.15 mm | 5 m | Water cooling | 98.44 |
| 35 | 10% | 2.36 | 29.56 | 3.15 mm | 10 m | 112° C. | 0.635 | 20.3 | 3.15 mm | 5 m | Water cooling | 98.58 |

There was a tendency that a more favorable result was obtained as the pressure in the tube was higher, but the influence of the pressure was not so remarkable.

It was noted that, the average pressure in the tube was from 0.044 to 0.694 MPa in all of Examples in the present specification.

EXAMPLES 36 TO 39

Next, the influence of the length of the tube of the tubular flow reactor 62 was investigated for the case of 10 m and the case of 15 m. The results are presented in the following Table 6.

There was a tendency that the residence time increased as the tube was longer and thus the conversion ratio also increased. However, it is preferable to adjust the length of the tube to an appropriate length but not too long from the viewpoint of economical efficiency.

EXAMPLES 40 TO 52

Next, the influence of the molar ratio of sodium chlorite to diethyl malonate was investigated. The bath temperature was 102° C. in Examples 40 to 45 and the bath temperature was 112° C. in Examples 46 to 50. The bath temperature was 102° C. and the flow rate was slowed down in Examples 51 and 52.

TABLE 6

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 36 | 10% | 2.21 | 30.43 | 3.15 mm | 10 m | 112° C. | 0.310 | 19.7 | 3.15 mm | 5 m | Water cooling | 98.19 |
| 37 | 10% | 2.10 | 30.36 | 3.15 mm | 15 m | 112° C. | 0.313 | 29.6 | 3.15 mm | 5 m | Water cooling | 99.59 |
| 38 | 10% | 2.24 | 37.79 | 3.15 mm | 10 m | 127° C. | 0.418 | 15.9 | 3.15 mm | 5 m | Water cooling | 97.78 |
| 39 | 10% | 2.26 | 29.34 | 3.15 mm | 15 m | 112° C. | 0.462 | 30.7 | 3.15 mm | 5 m | Water cooling | 99.73 |

The results are presented in the following Table 7.

TABLE 7

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 40 | 10% | 1.62 | 38.59 | 3.15 mm | 15 m | 102° C. | 0.224 | 23.3 | 3.15 mm | 5 m | Water cooling | 76.41 |
| 41 | 10% | 1.75 | 39.47 | 3.15 mm | 15 m | 102° C. | 0.219 | 22.8 | 3.15 mm | 5 m | Water cooling | 76.81 |
| 42 | 10% | 1.86 | 31.71 | 3.15 mm | 15 m | 102° C. | 0.152 | 28.4 | 3.15 mm | 5 m | Water cooling | 87.26 |
| 43 | 10% | 2.02 | 34.26 | 3.15 mm | 15 m | 102° C. | 0.182 | 26.3 | 3.15 mm | 5 m | Water cooling | 86.04 |
| 44 | 10% | 2.05 | 32.78 | 3.15 mm | 15 m | 102° C. | 0.139 | 27.5 | 3.15 mm | 5 m | Water cooling | 84.46 |
| 45 | 10% | 2.25 | 33.04 | 3.15 mm | 15 m | 102° C. | 0.188 | 27.2 | 3.15 mm | 5 m | Water cooling | 93.26 |
| 46 | 10% | 1.80 | 37.17 | 3.15 mm | 15 m | 112° C. | 0.355 | 24.2 | 3.15 mm | 5 m | Water cooling | 90.11 |
| 47 | 10% | 2.01 | 33.77 | 3.15 mm | 15 m | 112° C. | 0.290 | 26.6 | 3.15 mm | 5 m | Water cooling | 91.93 |
| 48 | 10% | 2.04 | 31.04 | 3.15 mm | 15 m | 112° C. | 0.273 | 29.0 | 3.15 mm | 5 m | Water cooling | 95.13 |
| 49 | 10% | 2.08 | 31.37 | 3.15 mm | 15 m | 112° C. | 0.278 | 28.7 | 3.15 mm | 5 m | Water cooling | 98.26 |
| 50 | 10% | 2.12 | 31.06 | 3.15 mm | 15 m | 112° C. | 0.267 | 29.0 | 3.15 mm | 5 m | Water cooling | 97.28 |
| 51 | 10% | 2.07 | 17.93 | 3.15 mm | 15 m | 102° C. | 0.084 | 50.2 | 3.15 mm | 5 m | Water cooling | 99.34 |
| 52 | 10% | 3.03 | 14.96 | 3.15 mm | 15 m | 102° C. | 0.052 | 60.1 | 3.15 mm | 5 m | Water cooling | 95.83 |

The results indicate that the conversion ratio tends to increase as the molar ratio is greater and that it is sufficient to have a molar ratio of about 2. As can be seen in Example 52, the conversion ratio in a case in which the molar ratio was 3 or more and the flow rate was slowed down was the same as that in the case of having a molar ratio of about 2.

EXAMPLES 53 TO 56

Next, the experiment was conducted by setting the length of the tube of the tubular flow reactor 62 to 5 m. The length of the tube was 10 m in Example 53 but was set to 5 m under the same conditions in Examples 54 to 56. However, the flow rate was slowed down in order to increase the residence time to 10 seconds or longer.

The results are presented in the following Table 8.

TABLE 8

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 53 | 10% | 2.10 | 31.16 | 3.15 mm | 10 m | 112° C. | 0.227 | 19.3 | 3.15 mm | 5 m | Water cooling | 87.77 |
| 54 | 10% | 2.19 | 28.71 | 3.15 mm | 5 m | 112° C. | 0.134 | 10.4 | 3.15 mm | 5 m | Water cooling | 1.57 |
| 55 | 10% | 2.78 | 29.68 | 3.15 mm | 5 m | 112° C. | 0.298 | 10.1 | 3.15 mm | 5 m | Water cooling | 3.80 |
| 56 | 10% | 1.82 | 9.28 | 3.15 mm | 5 m | 112° C. | 0.044 | 32.3 | 3.15 mm | 5 m | Water cooling | 27.65 |

As a result, it has been found out that the reaction proceeds even when the length of the tube is 5 m, but the conversion ratio may not be sufficient in some cases. Although the detailed reason for this is not clear, it is considered that this reaction is not proceeded in the entire region of the tube of the tubular flow reactor 62 but the preparation to enter the activated state, which is necessary to initiate the reaction, proceeds at the inlet portion of the tubular flow reactor 62. It is considered that the reaction is initiated at the stage that the preparation is completed. Hence, it is considered that this reaction is not immediately initiated when the raw material compounds are mixed and heated but is a reaction that requires a certain induction period.

The presence of this induction period is not particularly concerned in a batch reaction but has been found to be a significantly important factor in the case of a continuous reaction. It is considered that the reason for that a favorable result has not been obtained in Comparative Examples 1 and 2 described above is also probably because the induction period cannot be maintained.

Consequently, from the results of these Examples, it is considered that a tube with a certain length is required in order to maintain the induction period in the case of conducting the reaction in a continuous manner. In the present specification, the portion for maintaining the induction period is named the "temperature rising part". For this, it is considered that the total length of the tube of the tubular flow reactor 62 can be divided into the "temperature rising part" required to maintain the induction period and the "reaction part" of the portion at which the reaction is initiated after the induction period.

EXAMPLES 57 TO 60

In the apparatus used until Example 56, the reaction mixture cooled in the tubular flow reactor 63 directly flowed out therefrom. However, this reaction mixture contains not only unreacted sodium chlorite but also gaseous chlorine dioxide of a byproduct, and these are discharged at the same time. There is a risk of explosion when gaseous chlorine dioxide is discharged and chlorine dioxide is accumulated at a high concentration. In addition, chlorine dioxide at a low concentration is also useful as a bleaching agent or a fungicide and a disinfectant but the discharge of chlorine dioxide at a high concentration would be undesirable for the environment as well. Accordingly, it was decided to provide a measure to quench these sodium chlorite and chlorine dioxide.

Figure 7:
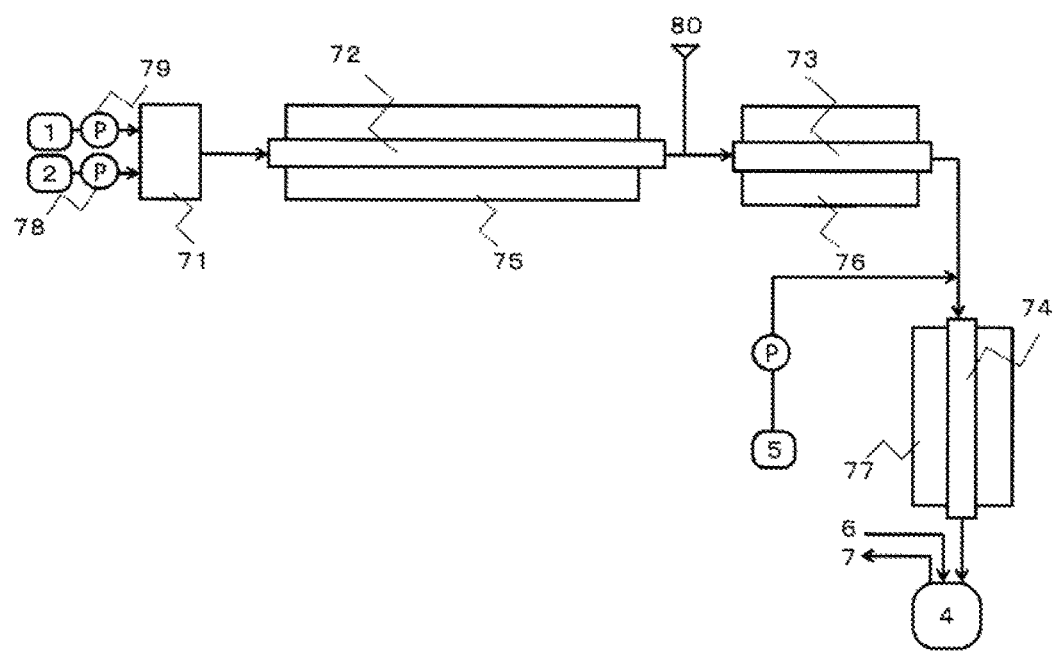
FIG. 7 schematically illustrates the outline of the reaction apparatus of the present invention used in Example 57 and the like. The mixture of raw material compounds is introduced into a tubular flow reactor 72 having a bath 75, subsequently introduced into a tubular flow reactor 73 having a water bath 76, the quench liquid from a container 5 is mixed with the reaction mixture discharged from the tubular flow reactor 73, and the mixture thus obtained is introduced into a tubular flow reactor 74 having a water bath 77. The reaction product discharged from the tubular flow reactor 74 passes through the pipe to be accumulated in a container 4.

The reaction apparatus used in the present Example is illustrated in FIG. 7.

A container 1 contains an aqueous solution of sodium chlorite of a raw material, and a container 2 contains a mixture of diethyl malonate and acetic acid of raw materials at a weight ratio of 5:1 (a molar ratio of 1:0.5). These raw materials are respectively supplied via pumps 79 and 78. Each of the raw materials thus supplied is mixed by a mixer 71. The mixture is introduced into a tubular flow reactor 72 made of a titanium tube with an inner diameter of 3.15 mm. The tubular flow reactor 72 is housed in a bath 75. The reaction mixture discharged from the tubular flow reactor 72 is then introduced into a tubular flow reactor 73 also made of a titanium tube with an inner diameter of 3.15 mm. The tubular flow reactor 73 is housed in a water bath 76 for water cooling. A quench liquid from a container 5 is mixed with the reaction mixture discharged from the tubular flow reactor 73 by a T-shaped tube, and the mixture thus obtained is introduced into a tubular flow reactor 74. The tubular flow reactor 74 is housed in a water bath 77 for water cooling. Thereafter, in the tubular flow reactor 74, unreacted sodium chlorite and chlorine dioxide of a byproduct in the reaction mixture react with the components of the quench liquid so as to decompose these sodium chlorite, chlorine dioxide and the like. The treated liquid that is discharged from the tubular flow reactor 74 passes through the pipe to be accumulated in a container 4. An inert gas such as nitrogen gas is blown from a pipe 6 into the container 4 and the gas in the container 4 is discharged from a pipe 7. All the tubes of the tubular flow reactor 72, the tubular flow reactor 73, and the tubular flow reactor 74 are wound into a coil shape. 80 is a safety valve.

The operating conditions of Examples 57 to 60 are presented in the following Table 9.

chlorite and sodium hydroxide at a molar ratio of 0.23 with respect to sodium chlorite was used as the quench liquid in Example 59. The treatment was performed in the water bath 77 under an ice-cold (5° C.) condition in the same manner as in Example 58. The chlorine dioxide gas was not detected from this treated liquid.

In addition, Example 60 in which a mixed aqueous solution containing sodium sulfite at a molar ratio of 0.51 with respect to sodium chlorite and sodium hydroxide at a molar ratio of 0.31 with respect to sodium chlorite was used as the quench liquid and the water bath 77 was in water cooling condition (25° C.), the chlorine dioxide gas was not detected from this treated liquid also as in Example 59.

Meanwhile, the chlorine dioxide gas was quantified by the oxidation-reduction titration (detection limit: 54.6 ppm), and sodium chlorite was quantified using the PACKTEST for sodium chlorite (Model: WAK-NaClO$_2$ manufactured by Kyoritsu Chemical-Check Lab., Corp.) (detection limit: 5 ppm).

In Examples 57 to 60, the temperature of the reaction mixture was measured in the vicinity of the outlet of the tubular flow reactor 72. The temperature of the reaction mixture in the vicinity of the outlet of the tubular flow reactor 72 was within the range of approximately from 95 to 150° C. after starting the operation, and it was possible to conduct the steady operation at mostly 140±5° C. Here, the bath is used for heating at least at the time of initiating the reaction. However, it is presumed that the bath functions for cooling in the latter half portion of the reactor tube.

TABLE 9

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 57 | 10% | 1.99 | 32.72 | 3.15 mm | 20 m | 112° C. | 0.694 | 36.7 | 3.15 mm | 5 m | Water cooling | 100 |
| 58 | 10% | 1.98 | 33.03 | 3.15 mm | 20 m | 112° C. | 0.691 | 36.3 | 3.15 mm | 5 m | Water cooling | 100 |
| 59 | 10% | 1.93 | 32.20 | 3.15 mm | 20 m | 112° C. | 0.673 | 37.3 | 3.15 mm | 5 m | Water cooling | 100 |
| 60 | 10% | 1.46 | 33.41 | 3.15 mm | 20 m | 112° C. | 0.562 | 35.9 | 3.15 mm | 5 m | Water cooling | 95.43 |

In Example 57, an aqueous solution of sodium sulfite having a molar ratio of sodium sulfite to sodium chlorite of 0.57 was mixed as the quench liquid and cooled (25° C.) in the water bath 77, and the chlorine dioxide gas was not detected from the treated liquid as a result. However, in Example 58, an aqueous solution of sodium sulfite was mixed in the same amount as in Example 57, and the treatment was performed in the water bath 77 under an ice-cold (5° C.) condition. The chlorine dioxide gas was detected from this treated liquid.

EXAMPLES 61 TO 63

Next, the production experiments described in the following Table 10 were conducted using a tube with a diameter of 6 mm as the titanium tube of the tubular flow reactor 72 in the reaction apparatus illustrated in FIG. 7. As the quench liquid, a 1:1 mixture of a 20% aqueous solution of sodium sulfite and a 25% aqueous solution of sodium hydroxide was used.

The results are presented in Table 10.

TABLE 10

| Example No. | Concentration of sodium chlorite | Molar ratio | Mean flow rate (m/min) | Diameter of the reactor tube | Length of the reactor tube | Bath temperature | Average pressure (MPa) | Heat transfer time (seconds) | Diameter of the cooling tube | Length of the cooling tube | Temperature for cooling | Conversion ratio (%) |
|---|---|---|---|---|---|---|---|---|---|---|---|---|
| 61 | 10% | 2.19 | 18.24 | 6 mm | 20 m | 92° C. | 0.137 | 65.3 | 3 mm | 5 m | Water cooling | 97.57 |
| 62 | 10% | 2.14 | 21.52 | 6 mm | 20 m | 102° C. | 0.238 | 55.8 | 3 mm | 5 m | Water cooling | 98.89 |
| 63 | 10% | 2.11 | 21.50 | 6 mm | 20 m | 112° C. | 0.235 | 41.9 | 3 mm | 5 m | Water cooling | 100 |

As described above, only sodium sulfite is not necessarily sufficient, and thus a mixed aqueous solution containing sodium sulfite at a molar ratio of 0.38 with respect to sodium A tube with a diameter of 3.15 mm was used in Examples 57 to 60, but a tube with a diameter of 6 mm which was about two times the diameter of the tube used in Examples 57 to 60 was used in Examples 61 to 63. The reaction safely proceeded in the same manner although a tube with a diameter of 6 mm was used, and significantly favorable results were obtained.

This indicates that it is possible to produce a great quantity of a ketomalonic acid diester in an industrial scale in the continuous production method of the present invention.

INDUSTRIAL APPLICABILITY

The method of the present invention provides a process for continuous production of a ketomalonic acid compound or a hydrate thereof such as a ketomalonic acid diester which is used in the production of pharmaceuticals and agricultural chemicals as a substrate when producing a pyrazine-2-one-3-carboxylic acid ester derivative by reacting with a diamine and also as a raw material compound when producing a quinoxalinone derivative from an aromatic diamine. The method of the present invention is suitable for the efficient, safe and constant production of a ketomalonic acid diester represented by the general formula (2) or a hydrate thereof in a great quantity by an industrial process and is useful in the organic chemical industry including pharmaceuticals, agricultural chemicals and the like.

The invention claimed is:

1. A method for continuously producing a ketomalonic acid diester or a hydrate thereof, comprising:
    step (A) mixing a malonic acid diester, a carboxylic acid compound, and a chlorous acid compound to obtain a mixed mixture;
    step (B) supplying the mixed mixture to one or more tubular flow reactors; and
    step (C) reacting the mixed mixture in the one or more tubular flow reactors to obtain a reaction mixture;
    wherein the reaction mixture is continuously producing the ketomalonic acid diester or the hydrate thereof,
    wherein the length of the tube of the one or more tubular flow reactor is from 9 m to 50 m,
    wherein a temperature control part of the one or more tubular flow reactors controls the temperature of the one or more tubular flow reactors at 80° C. or higher.

2. The method according to claim 1, wherein the chlorous acid compound is supplied to step (A) as an aqueous solution of a chlorous acid compound.

3. The method according to claim 1, wherein the malonic acid diester or a mixture of the malonic acid diester and the carboxylic acid compound is supplied to step (A) in the absence of a solvent.

4. The method according to claim 1, wherein the temperature control part is a bath and the bath is at a temperature of 80° C. or higher.

5. The method according to claim 1, wherein the method further comprises:
    step (D) aging the reaction mixture obtained in the step (C).

6. The method according to claim 5, wherein the step (D) is performed in one or more second flow reactors.

7. The method according to claim 1, wherein the method further comprises:
    step (E) quenching the reaction by mixing a quench liquid with the reaction mixture obtained in the step (C).

8. The method according to claim 7, wherein the step (E) is performed in one or more third tubular flow reactors.

9. The method according to claim 7, wherein the quench liquid is an aqueous solution of a sulfite salt and/or an alkali metal hydroxide.

10. The method according to claim 1, wherein the malonic acid diester is a malonic acid diester having chemical formula (1)

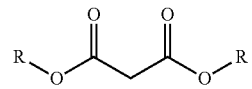

(1)

wherein, in the chemical formula (1), R may be the same as or different from each other and represents an alkyl group which optionally has substituent(s), a cycloalkyl group which optionally has substituent(s), an aromatic hydrocarbon group which optionally has substituent(s), or an aromatic heterocyclic group which optionally has substituent(s), or two Rs may bind to each other to form a ring with adjacent oxygen atoms.

11. The method according to claim 1, wherein the ketomalonic acid diester is a ketomalonic acid diester having chemical formula (2)

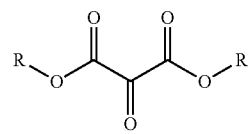

(2)

wherein, in the chemical formula (2), R may be the same as or different from each other and represents an alkyl group which optionally has substituent(s), a cycloalkyl group which optionally has substituent(s), an aromatic hydrocarbon group which optionally has substituent(s), or an aromatic heterocyclic group which optionally has substituent(s), or two Rs may bind to each other to form a ring with adjacent oxygen atoms.

12. The method according to claim 1, wherein the method is an industrial production method.

13. The method according to claim 5, wherein the method further comprises:
    step (E) quenching the reaction by mixing a quench liquid with the reaction mixture obtained in the step (D).

14. The method according to claim 13, wherein the step (E) is performed in one or more third tubular flow reactors.

15. The method according to claim 13, wherein the quench liquid is an aqueous solution of a sulfite salt and/or an alkali metal hydroxide.

16. The method according to claim 1, wherein the malonic acid diester is a malonic acid diester having chemical formula (1)

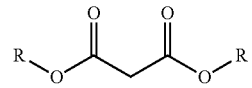

(1)

wherein, in the chemical formula (1), R may be the same as or different from each other and represents an alkyl group which optionally has substituent(s), a cycloalkyl group which optionally has substituent(s), an aromatic hydrocarbon group which optionally has substituent(s), or an aromatic heterocyclic group which optionally has substituent(s), or two Rs may bind to each other to form a ring with adjacent oxygen atoms; and wherein the ketomalonic acid diester is a ketomalonic acid diester having chemical formula (2)

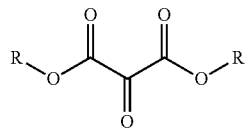

(2)

wherein, in the chemical formula (2), R may be the same as or different from each other and represents an alkyl group which optionally has substituent(s), a cycloalkyl group which optionally has substituent(s), an aromatic hydrocarbon group which optionally has substituent(s), or an aromatic heterocyclic group which optionally has substituent(s), or two Rs may bind to each other to form a ring with adjacent oxygen atoms.

* * * * *